(12) United States Patent
Smellie et al.

(10) Patent No.: US 9,535,583 B2
(45) Date of Patent: Jan. 3, 2017

(54) DRAW-AHEAD FEATURE FOR CHEMICAL STRUCTURE DRAWING APPLICATIONS

(71) Applicant: PerkinElmer Informatics, Inc., Waltham, MA (US)

(72) Inventors: Andrew Smellie, Candia, NH (US); Mark L. Olson, Framingham, MA (US)

(73) Assignee: PERKINELMER INFORMATICS, INC., Waltham, MA (US)

( * ) Notice: Subject to any disclaimer, the term of this patent is extended or adjusted under 35 U.S.C. 154(b) by 718 days.

(21) Appl. No.: 13/714,307

(22) Filed: Dec. 13, 2012

(65) Prior Publication Data
US 2014/0173475 A1    Jun. 19, 2014

(51) Int. Cl.
*G06F 3/048* (2013.01)
*G06F 3/0484* (2013.01)
*G06F 19/00* (2011.01)

(52) U.S. Cl.
CPC ......... *G06F 3/04842* (2013.01); *G06F 19/708* (2013.01); *G06F 19/709* (2013.01)

(58) Field of Classification Search
CPC ...... G06F 19/708; G06F 19/12; G06F 19/701; G06F 3/14; G06F 17/30598; G06F 19/3431; G06F 19/709; G06F 3/04842
See application file for complete search history.

(56) References Cited

U.S. PATENT DOCUMENTS 4,967,372 A * 10/1990 Feldman ................ 715/203
5,008,831 A *  4/1991 Feldman ............ G06F 19/708
                                                 703/12

(Continued)

FOREIGN PATENT DOCUMENTS

EP    1526471 A1    4/2005
EP    2567338 A1    3/2013
(Continued)

OTHER PUBLICATIONS

Algorri et al. "Reconstruction of Chemical Molecules from Images," 2007 Annual International Conference of the IEEE Engineering in Medicine and Biology Society (EMBC '07), Lyon, France, Aug. 22-26, 2007, in Conjunction with the Biennial Conference of the Societe Francaise de Genie Biologique et Medical (SFGB), Aug. 22, 2007, pp. 4609-4612.
(Continued)

*Primary Examiner* — Jennifer To
*Assistant Examiner* — Joseph R Burwell
(74) *Attorney, Agent, or Firm* — Choate, Hall & Stewart, LLP; William R. Haulbrook

(57) ABSTRACT

Systems, methods, and apparatus are provided that allow a user to draw and edit a chemical structure. Aspects of the present disclosure may include receiving an input corresponding to an amendment to a portion of an in-progress chemical structure, and identifying, based at least in part upon the amended in-progress chemical structure, one or more molecular scaffolds from a set of candidate molecular scaffolds. Each molecular scaffold may be configured to, upon one or both of (i) appending to the amended portion of the in-progress chemical structure and (ii) replacing or partially replacing the amended portion of the in-progress chemical structure, provide a resulting chemical structure or chemical structure fragment that has been previously rendered. The one or more molecular scaffolds may be provided for presentation on the graphical display as option(s) for selection by a user in creating the graphical representation of the chemical structure.

33 Claims, 7 Drawing Sheets

(56) References Cited

U.S. PATENT DOCUMENTS

| | | | |
|---|---|---|---|
| 5,249,137 A | 9/1993 | Wilson et al. | |
| 5,386,507 A * | 1/1995 | Teig et al. | 715/836 |
| 5,434,971 A | 7/1995 | Lysakowski, Jr. | |
| 5,461,580 A * | 10/1995 | Facci | G06T 17/00 703/2 |
| 6,017,390 A | 1/2000 | Charych et al. | |
| 6,304,869 B1 * | 10/2001 | Moore et al. | 702/27 |
| 6,434,490 B1 | 8/2002 | Agrafiotis et al. | |
| 6,582,233 B1 * | 6/2003 | Clark | G06T 11/206 434/277 |
| 7,250,950 B2 | 7/2007 | Smith et al. | |
| 7,613,574 B2 | 11/2009 | Verseput | |
| 7,650,327 B2 | 1/2010 | Remsen et al. | |
| 7,663,607 B2 | 2/2010 | Hotelling et al. | |
| 7,676,499 B2 | 3/2010 | Dorsett, Jr. | |
| 7,705,830 B2 | 4/2010 | Westerman et al. | |
| 7,707,206 B2 | 4/2010 | Encina et al. | |
| 7,805,437 B1 | 9/2010 | Andersson et al. | |
| 7,912,689 B1 * | 3/2011 | Helson | G06F 19/708 703/12 |
| 8,407,578 B2 | 3/2013 | Boyer et al. | |
| 8,433,723 B2 | 4/2013 | Smith et al. | |
| 8,538,983 B2 | 9/2013 | Huang et al. | |
| 2002/0049548 A1 * | 4/2002 | Bunin | 702/32 |
| 2002/0051999 A1 * | 5/2002 | Sepetov et al. | 702/27 |
| 2002/0107359 A1 | 8/2002 | Hogarth et al. | |
| 2002/0161599 A1 | 10/2002 | Faerman et al. | |
| 2003/0194687 A1 * | 10/2003 | Clark | 434/278 |
| 2004/0003000 A1 * | 1/2004 | Smith | G06F 19/702 |
| 2004/0006742 A1 | 1/2004 | Slocombe | |
| 2004/0024493 A1 * | 2/2004 | Fagrell et al. | 700/266 |
| 2004/0088118 A1 * | 5/2004 | Jensen et al. | 702/30 |
| 2004/0122641 A1 * | 6/2004 | Miller et al. | 703/12 |
| 2004/0171062 A1 * | 9/2004 | Hirth et al. | 702/19 |
| 2004/0236740 A1 | 11/2004 | Cho et al. | |
| 2004/0249791 A1 | 12/2004 | Waters et al. | |
| 2005/0010603 A1 * | 1/2005 | Berks | G06F 19/708 |
| 2005/0094205 A1 * | 5/2005 | Lo et al. | 715/505 |
| 2005/0102313 A1 | 5/2005 | Levering et al. | |
| 2005/0123993 A1 | 6/2005 | Brunner et al. | |
| 2005/0131894 A1 | 6/2005 | Vuong | |
| 2005/0177280 A1 * | 8/2005 | Almstetter et al. | 700/266 |
| 2005/0226495 A1 | 10/2005 | Li | |
| 2006/0040322 A1 * | 2/2006 | Archetti et al. | 435/7.1 |
| 2006/0061595 A1 | 3/2006 | Goede et al. | |
| 2006/0123113 A1 | 6/2006 | Friedman | |
| 2006/0277201 A1 | 12/2006 | Dorsett | |
| 2007/0016853 A1 | 1/2007 | Abagyan et al. | |
| 2007/0174765 A1 | 7/2007 | Schleppenbach et al. | |
| 2007/0177803 A1 | 8/2007 | Elias et al. | |
| 2007/0192747 A1 * | 8/2007 | Phelan | G06F 15/16 715/847 |
| 2007/0260583 A1 * | 11/2007 | Domine et al. | 707/3 |
| 2007/0276636 A1 * | 11/2007 | Wythoff | G06F 19/708 703/2 |
| 2008/0036743 A1 | 2/2008 | Westerman et al. | |
| 2008/0136785 A1 * | 6/2008 | Baudisch et al. | 345/173 |
| 2008/0140616 A1 | 6/2008 | Encina et al. | |
| 2008/0165140 A1 | 7/2008 | Christie et al. | |
| 2008/0213663 A1 | 9/2008 | Hu et al. | |
| 2008/0228774 A1 | 9/2008 | Hamilton et al. | |
| 2008/0234996 A1 * | 9/2008 | Ghosh | G06F 19/706 703/12 |
| 2008/0309632 A1 | 12/2008 | Westerman et al. | |
| 2009/0006411 A1 | 1/2009 | Lele et al. | |
| 2009/0063427 A1 | 3/2009 | Zuta et al. | |
| 2009/0171975 A1 | 7/2009 | McConnell et al. | |
| 2009/0273571 A1 | 11/2009 | Bowens | |
| 2010/0257457 A1 | 10/2010 | De Goes | |
| 2011/0163944 A1 | 7/2011 | Bilbrey et al. | |
| 2011/0221656 A1 | 9/2011 | Haddick et al. | |
| 2011/0276589 A1 | 11/2011 | Smith et al. | |
| 2012/0019488 A1 | 1/2012 | McCarthy | |
| 2012/0078853 A1 * | 3/2012 | Huang | G06F 17/30424 707/667 |
| 2012/0110486 A1 | 5/2012 | Sirpal et al. | |
| 2012/0154440 A1 * | 6/2012 | Nicholls | G06F 19/708 345/633 |
| 2012/0173622 A1 | 7/2012 | Toledano et al. | |
| 2012/0185513 A1 * | 7/2012 | Samukawa | G06F 19/709 707/796 |
| 2012/0188147 A1 | 7/2012 | Hosein et al. | |
| 2012/0246228 A1 | 9/2012 | Udezue et al. | |
| 2012/0284638 A1 | 11/2012 | Cutler et al. | |
| 2012/0311038 A1 | 12/2012 | Trinh et al. | |
| 2012/0324368 A1 | 12/2012 | Putz et al. | |
| 2013/0044042 A1 | 2/2013 | Olsson et al. | |
| 2013/0061163 A1 * | 3/2013 | Clark et al. | 715/771 |
| 2013/0218878 A1 | 8/2013 | Smith et al. | |
| 2013/0222265 A1 | 8/2013 | Smith et al. | |
| 2014/0089329 A1 * | 3/2014 | Kozloski et al. | 707/749 |
| 2014/0267240 A1 | 9/2014 | Smith | |
| 2014/0282106 A1 | 9/2014 | Smith et al. | |
| 2014/0337725 A1 | 11/2014 | Smith et al. | |
| 2015/0112604 A1 | 4/2015 | Smith | |
| 2015/0142730 A1 * | 5/2015 | Dakshanamurthy | G06F 19/324 707/609 |
| 2015/0199797 A1 | 7/2015 | Palo | |

FOREIGN PATENT DOCUMENTS

| | | |
|---|---|---|
| GB | 2493830 A | 2/2013 |
| WO | WO-2007092842 A2 | 8/2007 |
| WO | WO-2011140148 A1 | 11/2011 |
| WO | WO-2013126077 A1 | 8/2013 |

OTHER PUBLICATIONS

Casey et al. "Optical Recognition of Chemical Graphics," Document Analysis and Recognition, 1993, Proceedings of the Second International Conference on, Tsukuba Science City, Japan, Oct. 20-22, 1993, Los Alamitos, CA, USA, IEEE Comput. Soc., Oct. 20, 1993, pp. 627-631.

Filippov et al. "Optical Structure Recognition Software to Recover Chemical Information: OSRA, An Open Source Solution," Journal of Chemical Information and Modeling, vol. 49, No. 3, Mar. 23, 2009, pp. 740-743.

Park et al. "Automated extraction of chemical structure information from digital raster images," Chemistry Central Journal, Biomed Central Ltd., vol. 3, No. 1, Feb. 5, 2009, pp. 1-16.

Valko et al. "CLiDE Pro: The Latest Generation of CLiDE, a Tool for Optical Chemical Structure Recognition," Journal of Chemical Information and Modeling, vol. 49, No. 4, Mar. 19, 2009, pp. 780-787.

CambridgeSoft, Inc., Chem & Bio Draw, Version 12.0, 24 pages, 2009.

CambridgeSoft, Inc., ChemDraw User's Guide, Version 9.0.1, 23 pages, 2004.

ChemJuice Grande-Basic Structure Drawing, printout page of YouTube video posting from IOBS at http://www.youtube.com/watch?v=mKOcC5bLzdO, <http://www.youtube.com/watch?v=mKOcC5bLzdO>uploaded Oct. 3, 2011, printed May 18, 2015, 2 pages.

IDBS Makes Chemical Structure Drawing Mobile, Press Release, ID Business Solutions, Ltd., 2 pages, Dec. 9, 2009.

Logtenberg, Jeroen, Multi-user interaction with molecular visualizations on a multi-touch table, MSc thesis, Human Media Interaction Group, University of Twente, 48 pages, Aug. 11, 2009.

Mills, Nancy, ChemDraw Ultra 10.0, Journal of American Chemical Society, 128(41):13649-13650, 2006.

Mobile Molecular DataSheet, http://molmatinf.com/mmdsios.html, <http://molmatinf.com/mmdsios.html>Molecular Materials Informatics, Inc., Sep. 23, 2011, retrieved by Archive.org as https://web.archive.org/web/20120403140454/http:l/molmatinf.com/mmdsios.html on Apr. 3, 2012, 4 pages.

MoiPrime+, http://molmatinf.com/molprimeplus.html, <http://molmatinf.com/molprimeplus.html>Molecular Materials Informatics, Inc., Jan. 23, 2011, 13 pages.

(56) References Cited

OTHER PUBLICATIONS

International Search Report, PCT/US2012/026574, dated Mar. 20, 2013, 4 pgs.
Kim, et al, Development of a Gesture-Based Molecular Visualization Tool Based on Virtual Reality for Molecular Docking, Bull. Korean Chem. Soc. 2004, vol. 25, No. 10 pp. 1571-1574.
Williams, et al., Mobile apps for chemistry in the world of drug discovery, Drug Discovery Today, vol. 16. Nos. 21/22, Nov. 2011, pp. 928-939.
Williams, et al, Smart Phones, a Powerful Tool in the Chemistry Classroom, Journal of Chemical Education, 2011, pp. 683-686.
Wobbrock et al, User-Defined Gestures for Surface Computing, CHI—Tabletop Gestures, Apr. 7, 2009, pp. 1083-1092.
Written Opinion, PCT/US2012/026574, dated Mar. 20, 2013, 8 pgs.
Carmigniani, J. et al., Augmented Reality Technologies, Systems and Applications, Multimedia Tools and Applications 51:341-377, (2011).
Clark A. M., Basic Primitives for Molecular Diagram Sketching, Journal of Cheminformatics 2:8 (2010).
European Search Report for 13275308.8, Apr. 9, 2014, 4 pages.
European Search Report for 13275308.8, Aug. 13, 2014, 8 pages.
Furlon, Rod, Build Your Own Google Glass, Resources Hands on, IEEE Spectrum, IEEE Inc., vol. 50, No. 1, pp. 20-21, (Jan. 1, 2013).
Giudice N. A. et al., Learning Non-Visual Graphical Information Using a Touch-Based Vibro-Audio Interface, Proceedings of the 14th International ACM Sigaccess Conference on Computers and Accessibility, Assets '12, 103-110 (Jan. 1, 2012).
International Search Report for PCT/US2014/016249, Aug. 13, 2014, 4 pages.
International Search Report for PCT/US2014/035685, Aug. 4, 2014, 4 pages.
Li et al., Personal Experience with Four Kinds of Chemical Structure Drawing Software: Review on ChemDraw, ChemWindow, ISIS/Draw, and ChemSketch, J. Chem. Inf. Comput. Sci. 44:1886-1890 (2004).
Shine et al., ChemPad3 a tutorial, May 21, 2008, 10 pages.
Toennies J. L. et al., Toward Haptic/Aural Touchscreen Display of Graphical Mathematics for the Education of Blind Students, WHC, IEEE, 373:378 (2011).
Written Opinion for PCT/US2014/016249, Aug. 13, 2014, 7 pages.
Written Opinion for PCT/US2014/035685, Aug. 4, 2014, 8 pages.
International Search Report for PCT Application No. PCT/US2011/035070, mailed Oct. 6, 2011, 4 pages.
Written Opinion for PCT Application No. PCT/US2011/035070, mailed Oct. 6, 2011, 9 pages.
First Office Action for Chinese Application No. 201190000597.X, mailed May 29, 2013, 4 pages Including Translation.
Park et al. Tunable Machine Vision-Based Strategy for Automated Annotation of Chemical Databases, Journal of Chemical Information and Modeling, vol. 49, No. 8, 2009, pp. 1993-2001.
Jurach, T., Microsoft Outlook Quick Start Email Guide!, 1-3 (2006).
Lorensen et al., Marching Cubes: A high resolution 3D surface construction algorithm. In: Computer Graphics, vol. 21, Nr. 4, Jul. 1987.
Bennett, Samsung's AllShare Play pushes pictures from phone to cloud and TV, <http://news.cnet.com/8301-1035_3-57391735-94/samsungs-allshare-play-pushes-pictures-from-phone-to-cloud-and-tv/> [retrieved Oct. 24, 2013], Mar. 6, 2012, 9 pages.
Flick—Simply the easiest way to share, <http://getflick.io/> [retrieved Aug. 23, 2013], 4 pages.
Gonzalez-Villanueva et al., WallShare: A Collaborative Multi-pointer System for Portable Devices, Nov. 19, 2012, 7 pages.
iTunes Preview, Flick for iPhone, iPad, and iPod touch on the iTunes App Store, <https://itunes.apple.com/us/app/flick./id644265534?mt=8> [retrieved Oct. 28, 2013], 2 pages.
Layar, What is Layar?, <http://www.layar.com/features/> [retrieved Nov. 14, 2012], 7 pages.
Lucero et al., Pass-Them-Around: Collaborative Use of Mobile Phones for Photo Sharing, CHI 2011—Session: Photo Sharing, May 7-11, 2011, Vancouver, BC, Canada, 10 pages.
Pering et al., Enabling Pervasive Collaboration with Platform Composition, Intel Research Santa Clara, 2009, 18 pages.
Pering et al., Spontaneous Marriages of Mobile Devices and Interactive Spaces, Communications of the ACM, Sep. 2005, vol. 48, No. 9, pp. 53-59, 7 pages.
Scheible et al., MobiToss: A Novel gesture based interface for creating and sharing mobile multimedia art on large public displays, MM'08, Oct. 26-31, 2008 Vancouver British Columbia, Canada, pp. 957-960, 4 pages.
TSOTSIS, Word Lens Translates Words Inside of Images. Yes Really., <http://techcrunch.com/2010/12/16/world-lens-translates-words-inside-of-images-yes-really/> [retrieved Nov. 14, 2012], Dec. 16, 2010, 3 pages.
Weinberg et al., ZooZBeat: a Gesture-based Mobile Music Studio, NIME 2009, pp. 312-315, 4 pages.
Australian Patent Application No. 2011248243, APO Examination Report No. 1, issued Nov. 5, 2013, 3 pages.
"Introduction to Drawing (iPhone)", http://molmatinf.com/introdrawios.html, Molecular Materials Informatics, Inc., Dec. 9, 2010, retrieved by Archive.org as https://web.archive.org/web/20120413131358/http://molmatinf.com/introdrawios.html on Apr. 13, 2012.
"Overview of Drawing Gestures (iPhone)", http://molmatinf.com/gesturesios.html, Molecular Materials Informatics, Inc., Nov. 3, 2010, retrieved by Archive.org as https://web.archive.org/web/201001118005114/http://molmatinf.com/gesturesios.html on Nov. 18, 2010.

* cited by examiner

DRAW-AHEAD FEATURE FOR CHEMICAL STRUCTURE DRAWING APPLICATIONS

BACKGROUND

Chemical structure rendering software is widely used by research and educational institutions to depict chemical structures and chemical reactions of interest. Unlike chemical formulas or chemical names, structural formulas provide a graphical representation of the molecular structure. A graphical chemical structure representation is capable of indicating the arrangements of atoms in a way that a chemical formula cannot.

Current methods for drawing and editing chemical structures on a computer utilize mouse-driven or touch pad commands that include pointing and clicking on displayed menu items in a graphical user interface. Existing chemical structure rendering applications for handheld electronic devices such as tablet computers and portable phones utilize the same menu-driven paradigm. These applications can be clumsy when attempting to draw complex chemical structures including many separate elements.

SUMMARY OF THE INVENTION

Described herein are various embodiments of systems, methods, and apparatus that allow a user to electronically draw and edit a chemical structure. By offering a user pre-drawn portions of the chemical structure in a user-friendly, intuitive way, the systems, methods, and apparatus described herein provide efficient and accurate tools for drawing and editing chemical structures.

In various embodiments, the systems, methods, and apparatus utilize or include a tablet computer, a mobile phone device, or any other computer device or system capable of receiving input. The systems, methods, and apparatus have applications in a wide variety of industries that create and edit structural formulas, such as the reagent industry, the publishing industry, and/or the web search industry.

Elements of embodiments described with respect to a given aspect of the invention may be used in various embodiments of another aspect of the invention. For example, it is contemplated that features of dependent claims depending from one independent claim can be used in apparatus, articles, systems, and/or methods of any of the other independent claims.

In one aspect of the present disclosure, an apparatus for creating a graphical representation of a chemical structure using a draw-ahead feature includes a memory for storing a set of instructions and a processor for executing the set of instructions, where the instructions, when executed, cause the processor to provide a representation of at least a portion of an in-progress chemical structure for presentation on a graphical display, receive an input corresponding to an amendment to the portion of the in-progress chemical structure, identify, based at least in part upon the amended in-progress chemical structure, one or more molecular scaffolds from a set of candidate molecular scaffolds. Each molecular scaffold of the one or more molecular scaffolds may be configured to, upon one or both of (i) appending to the amended portion of the in-progress chemical structure and (ii) replacing or partially replacing the amended portion of the in-progress chemical structure, provide a resulting chemical structure or chemical structure fragment that has been previously rendered. The instructions, when executed, may cause the processor to provide the one or more molecular scaffolds for presentation on the graphical display as option(s) for selection by a user in creating the graphical representation of the chemical structure.

In some embodiments, the instructions, when executed, further cause the processor to, prior to providing the one or more molecular scaffolds for presentation, determine that a total number of the one or more molecular scaffolds does not exceed a threshold number of molecular scaffolds. The instructions, when executed, may cause the processor to receive an indication of user selection of a first molecular scaffold of the one or more molecular scaffolds provided, and append the first molecular scaffold to the portion of the in-progress chemical structure or replace or partially replace the amended portion of the in-progress chemical structure with the first molecular scaffold.

In some embodiments, the one or more molecular scaffolds include one or more commonly used molecular scaffolds. The commonly used molecular scaffolds may be scaffolds input and/or selected by a user or group of users at least a threshold number of times. The one or more molecular scaffolds may include one or more molecular scaffolds selected from an active database of candidate scaffolds.

In some embodiments, the instructions, when executed, cause the processor to arrange the one or more molecular scaffolds in a ranked order prior to providing the one or more molecular scaffolds for presentation on the graphical display. Arranging the one or more molecular scaffolds in the ranked order may include identifying a usage count associated with each molecular scaffold of the one or more molecular scaffolds. Arranging the one or more molecular scaffolds in the ranked order may include matching a user identifier associated with at least one molecular scaffold of the one or more molecular scaffolds to a user identifier associated with the portion of the chemical structure.

In some embodiments, receiving the input includes receiving the input, over a network, from a computing device. The one or more molecular scaffolds may be stored in the memory. The one or more molecular scaffolds may be stored in a database.

In one aspect of the present disclosure, a non-transitory computer readable medium has instructions stored thereon that, when executed, cause a processor to provide a representation of at least a portion of an in-progress chemical structure for presentation on a graphical display, and receive an input corresponding to an amendment to the portion of the in-progress chemical structure. The instructions may cause the processor to identify, based at least in part upon the amended in-progress chemical structure, one or more molecular scaffolds from a set of candidate molecular scaffolds, where each molecular scaffold of the one or more molecular scaffolds is configured to, upon one or both of (i) appending to the amended portion of the in-progress chemical structure and (ii) replacing or partially replacing the amended portion of the in-progress chemical structure, provide a resulting chemical structure or chemical structure fragment that has been previously rendered. The instructions may cause the processor to provide the one or more molecular scaffolds for presentation on the graphical display as option(s) for selection by a user in creating the graphical representation of the chemical structure.

In some embodiments, the portion of the in-progress chemical structure is all of the in-progress chemical structure.

In one aspect of the present disclosure, a method of creating a graphical representation of a chemical structure using a draw-ahead feature includes providing a representation of at least a portion of an in-progress chemical structure for presentation on a graphical display, and receiving an input corresponding to an amendment to the portion of the in-progress chemical structure. The method may include identifying, based at least in part upon the amended in-progress chemical structure, one or more molecular scaffolds from a set of candidate molecular scaffolds, where each molecular scaffold of the one or more molecular scaffolds is configured to, upon one or both of (i) appending to the amended portion of the in-progress chemical structure and (ii) replacing or partially replacing the amended portion of the in-progress chemical structure, provide a resulting chemical structure or chemical structure fragment that has been previously rendered. The method may include providing the one or more molecular scaffolds for presentation on the graphical display as option(s) for selection by a user in creating the graphical representation of the chemical structure.

In some embodiments, the user computing device is the computing device. The amendment may include addition of at least one of an atom, hydrocarbon ring, hydrocarbon chain, bond, and/or substituent. The amendment may include removal of at least one of an atom, hydrocarbon ring, hydrocarbon chain, bond, and/or substituent.

In one aspect of the present disclosure, a method for populating a set of candidate molecular scaffolds for use with a utility for creating a graphical representation of a chemical structure with a draw-ahead feature includes receiving a graphical representation of at least part of a chemical structure, and identifying, by a processor of a computing device, at least a first portion of the chemical structure as a molecular scaffold candidate for use with the utility for creating a graphical representation of a chemical structure with a draw-ahead feature, where the first portion of the chemical structure is determined to meet a minimum size requirement. The method may include determining, by the processor, that no match to the molecular scaffold candidate currently exists in the set of stored candidate molecular scaffolds, and adding, by the processor, the molecular scaffold candidate to the existing set of stored candidate molecular scaffolds.

In some embodiments, the first portion of the chemical structure is the entire chemical structure.

In some embodiments, identifying the first portion of the chemical structure as a molecular scaffold candidate may include pruning one or more excess elements from the received part of the chemical structure. The one or more excess elements may include at least one of a superatom and an unnatural fragment. The unnatural fragment may be pruned through application of a salt stripping algorithm. Pruning one or more excess elements may include simplifying the bond order of the received part of the chemical structure. Bond order simplification may include removing stereochemistry from the received part of the chemical structure. Pruning one or more excess elements may include atom simplification of the received part of the chemical structure. Atom simplification may include replacing all or some non-hydrogen atoms of the received part of the chemical structure with an exemplar element.

In some embodiments, determining that no match currently exists in the set of stored candidate molecular scaffolds includes querying a database containing the set of stored candidate molecular scaffolds. The method may further include identifying, by the processor, a second portion of the chemical structure as a second molecular scaffold candidate, determining, by the processor, that a matching candidate molecular scaffold to the second molecular scaffold candidate exists in the existing set of candidate molecular scaffolds, and incrementing a usage count associated with the matching candidate molecular scaffold.

In some embodiments, receiving the graphical representation of the at least part of the chemical structure includes importing the chemical structure from an electronic laboratory notebook (ELN) system. Receiving the graphical representation of the at least part of the chemical structure may include receiving the graphical representation of the chemical structure from a registration system having identified and stored the graphical representation of the chemical structure.

BRIEF DESCRIPTION OF THE DRAWINGS

The foregoing and other objects, aspects, features, and advantages of the invention will become more apparent and may be better understood by referring to the following description taken in conjunction with the accompanying drawings, in which:

FIGS. 4A and 4B illustrate example screen shots depicting a candidate molecular scaffold being presented to a user as a draw-ahead option based upon a portion of a graphical representation of a chemical structure;

Figure 1:
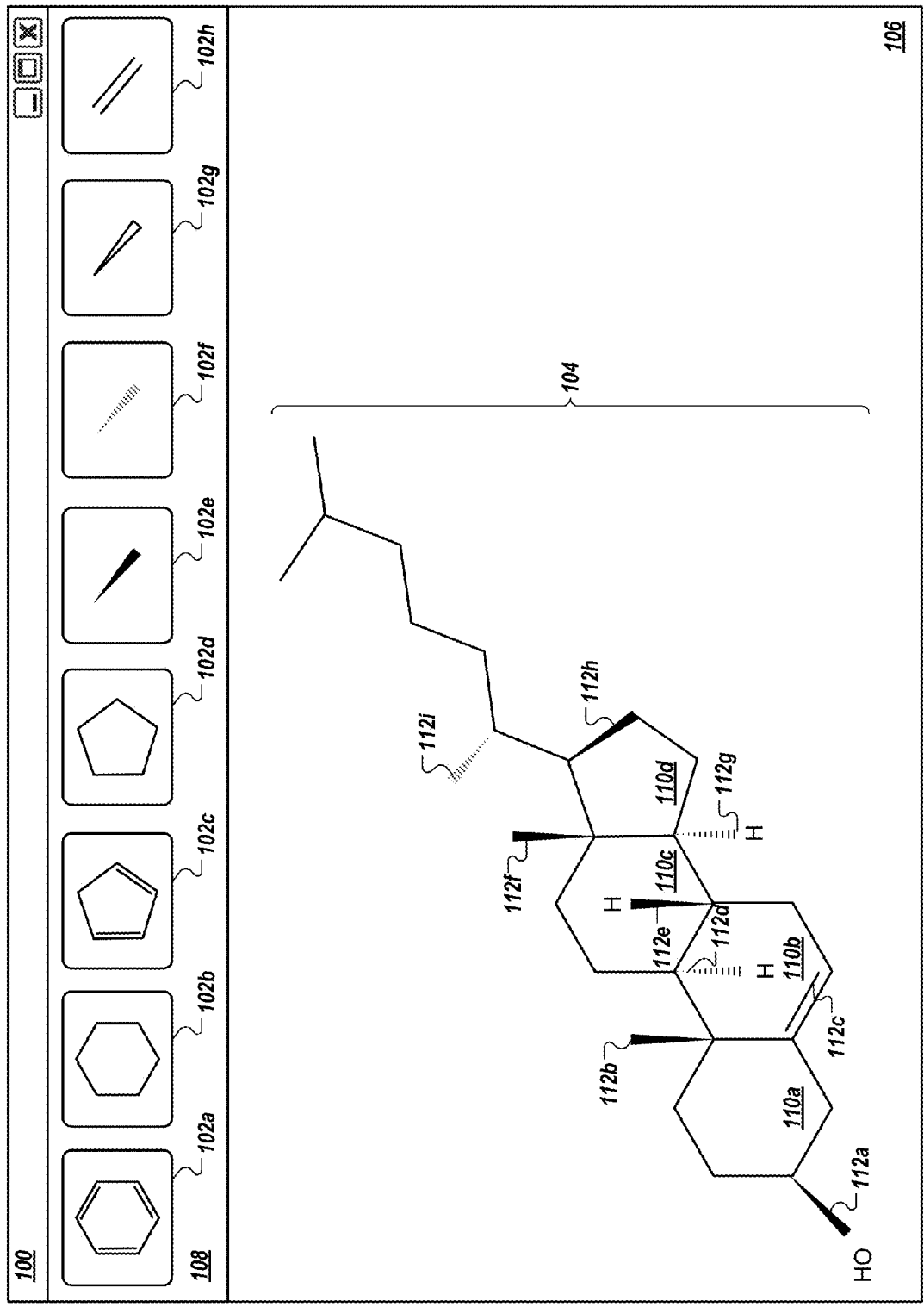
FIG. 1 is an example screen shot depicting a utility for creating or editing a graphical representation of a chemical structure.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DESCRIPTION

It is contemplated that apparatus, systems, and methods of the claimed invention encompass variations and adaptations developed using information from the embodiments described herein. Adaptation and/or modification of the apparatus, systems, and methods described herein may be performed by those of ordinary skill in the relevant art.

Throughout the description, where apparatus and systems are described as having, including, or comprising specific components, or where processes and methods are described as having, including, or comprising specific steps, it is contemplated that, additionally, there are apparatus and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

In general, in various embodiments, the present invention pertains to apparatus, systems, and methods for drawing chemical structures on a computing device. The computing device may be, for example, a personal computer, a workstation, a tablet computer (e.g., an Apple® IPad® by Apple Inc. of Cupertino, Calif.), or a mobile phone device. As used herein, the term "molecular scaffold" refers to a portion (e.g., a fragment) of a graphical representation of a chemical structure.

Referring to FIG. 1, a screen shot illustrates an example user interface 100 of a utility for creating and/or editing a graphical representation of a chemical structure. The user interface 100 includes a series of editing tools 102 for building a graphical representation of a chemical structure, e.g., a chemical structure 104 presented within an editing pane 106. A user, in some implementations, may select one of the editing tools 102 representing a ring of atoms, a bond, or a substituent, in order to place the selected ring, bond, or substituent in the chemical structure 104. For example, the user may click on one of the editing tools 102 and/or drag and drop the selected feature into the editing pane 106 to add the selected feature at a desired position within or on the current chemical structure 104.

In some implementations, a user may edit the chemical structure 104 by selecting a group of atoms (e.g., a ring of atoms) 110, a bond, or a substituent 112 in the chemical structure 104. The ring of atoms 110, bond, or substituent 112 location, in some examples, may be selected by clicking on a location on the chemical structure representation 104 with a mouse or other user interface device or by delivering a tap gesture upon a touch screen interface at a location of the chemical structure 104 which is to be amended. The user may then modify the chemical structure 104 at the selected ring of atoms 110, bond, or substituent 112 location by selecting one of the editing tools 102 from a menu 108. For example, the user may select a bond 112*h* within the chemical structure 104, then select a replacement bond (e.g., 102*f*) by tapping the user interface 100 at the location of the corresponding tool 102*f*. In other examples, the user may edit or add to the chemical structure 104 a heteroatom, a ring substituent, a multi-ring substituent, an acyclic chain, a chair cyclohexane, and/or any other molecular component. Additionally, the drawing/editing utility may determine whether or not a given edit would result in a structure that is chemically feasible and may limit executable edits to only those resulting in feasible chemical structures.

In some implementations, based upon a graphical representation of a chemical structure or a portion of a graphical representation of a chemical structure (e.g., a drawing in progress), a chemical structure fragment matching utility identifies one or more portions of the graphical representation of a chemical structure (e.g., as saved to a system via the chemical structure drawing utility) for presentation later as selectable molecular scaffolds to use when building or otherwise editing a graphical representation of a chemical structure. In this manner, for example, a user may be provided the opportunity to reuse portions of a current drawing or a former drawing when building or otherwise editing a graphical representation of a chemical structure, thereby saving time and preserving accuracy. In some implementations, molecular scaffolds derived from one or more graphical representations of chemical structures created by other users of the system may be presented as fragments to a particular user for building a graphical representation of a chemical structure.

Figure 2A:
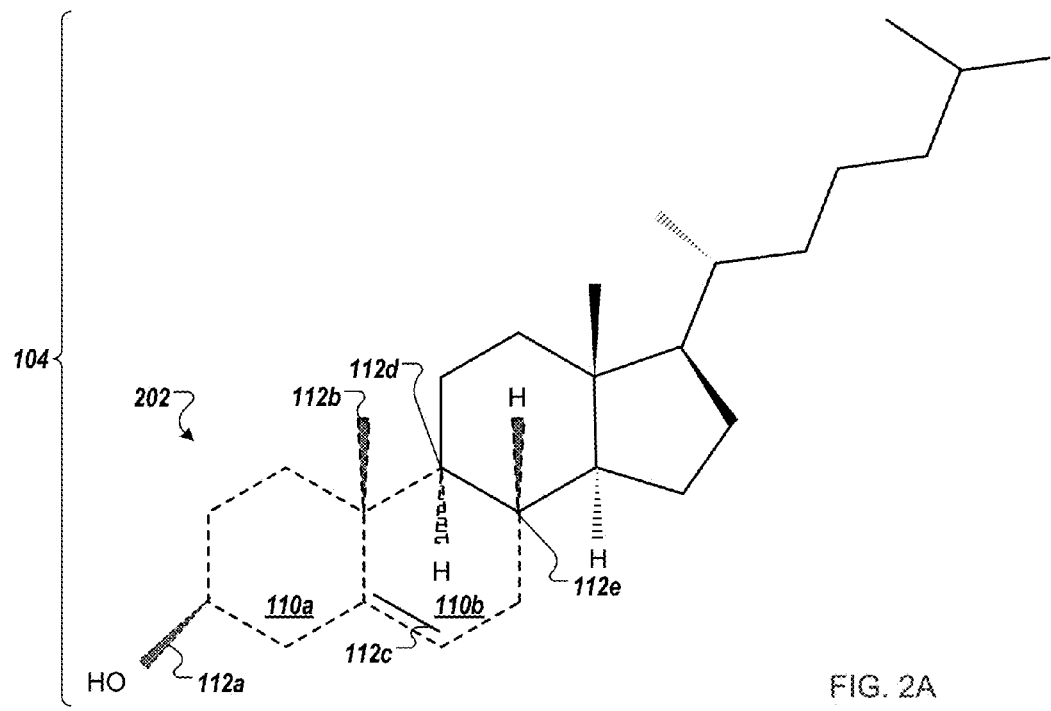
FIGS. 2A and 2B illustrate molecular scaffold identification from a portion of a graphical representation of a chemical structure.
Figure 2B:
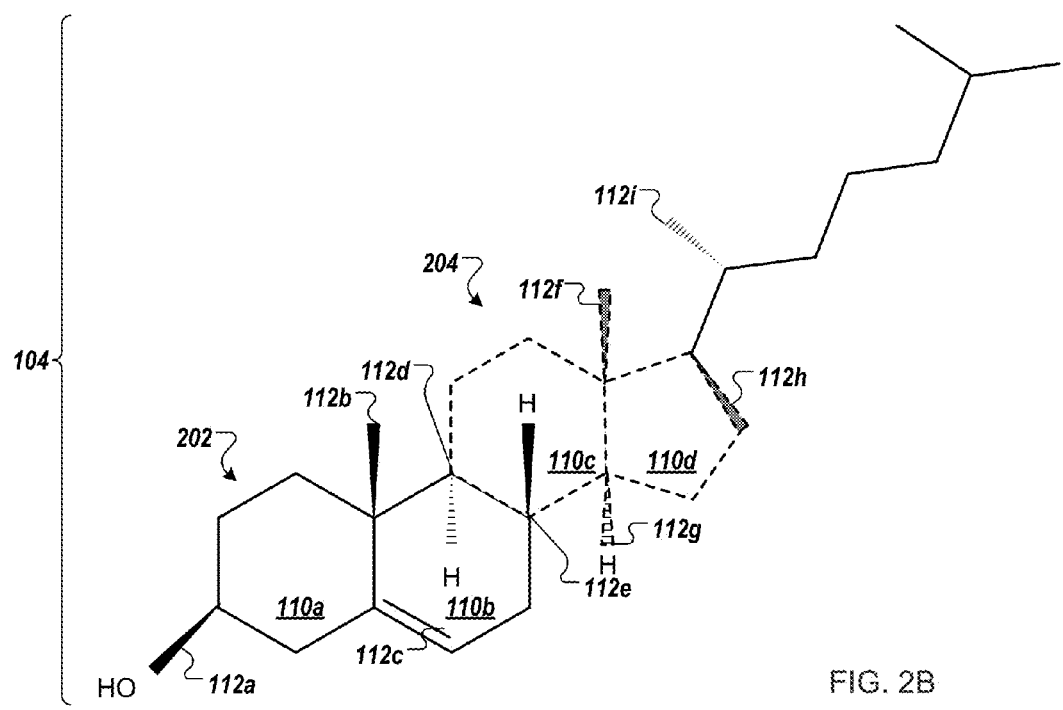

For example, turning to FIGS. 2A and 2B, an example of two different molecular scaffolds 202, 204 are illustrated in relation to the chemical structure 104. Each molecular scaffold 202, 204, for example, represents a fragment or portion of a graphical representation of a chemical structure. The chemical scaffolds 202, 204, in some implementations, include a combination of one or more hydrocarbon rings 110, chains, bonds, and substituents 112.

Turning to FIG. 2A, a first molecular scaffold 202 is identified by a dashed line. The first molecular scaffold 202, for example, includes rings 110*a* and 110*b*, as well as bonds/substituents 112*a*, 112*b*, 112*c*, 112*d*, and 112*e*.

Turning to FIG. 2B, a second molecular scaffold 204 is identified through a dashed line. The second molecular scaffold 204, for example, includes rings 110*c* and 110*d*, as well as bonds/substituents 112*f*, 112*g*, and 112*h*. Note that the hydrocarbon chain extending from ring 110*d* is not included as part of either the first molecular scaffold 202 or the second molecular scaffold 204. In some implementations, a portion of a chemical structure may be pruned from the fragment candidates prior to identifying each of the fragment candidates.

In the example shown in FIGS. 2A and 2B, the molecular scaffold 204 is identified as a partner scaffold to the molecular scaffold 202. For example, in a different drawing of a chemical structure, upon identification of the molecular scaffold 202 in that structure, it may be assumed that it is likely that additional atoms (e.g., yet to be drawn) may comprise the atoms of the molecular scaffold 204. In this manner, a draw-ahead utility may identify the first molecular scaffold 202 within a new graphical representation of a chemical structure and, in response, offer the second molecular scaffold 204 as a continuation of the drawing in progress.

In some implementations, the combination of two molecular scaffolds (e.g., molecular scaffold 202 and molecular scaffold 204) may be identified as a separate candidate fragment (e.g., a "super fragment," combining two smaller fragments). For example, within a graphical representation of a large chemical structure, varying sizes of sub-structures may be identified as fragments which are likely to reoccur in the graphical representation of different chemical structures.

Figure 3:
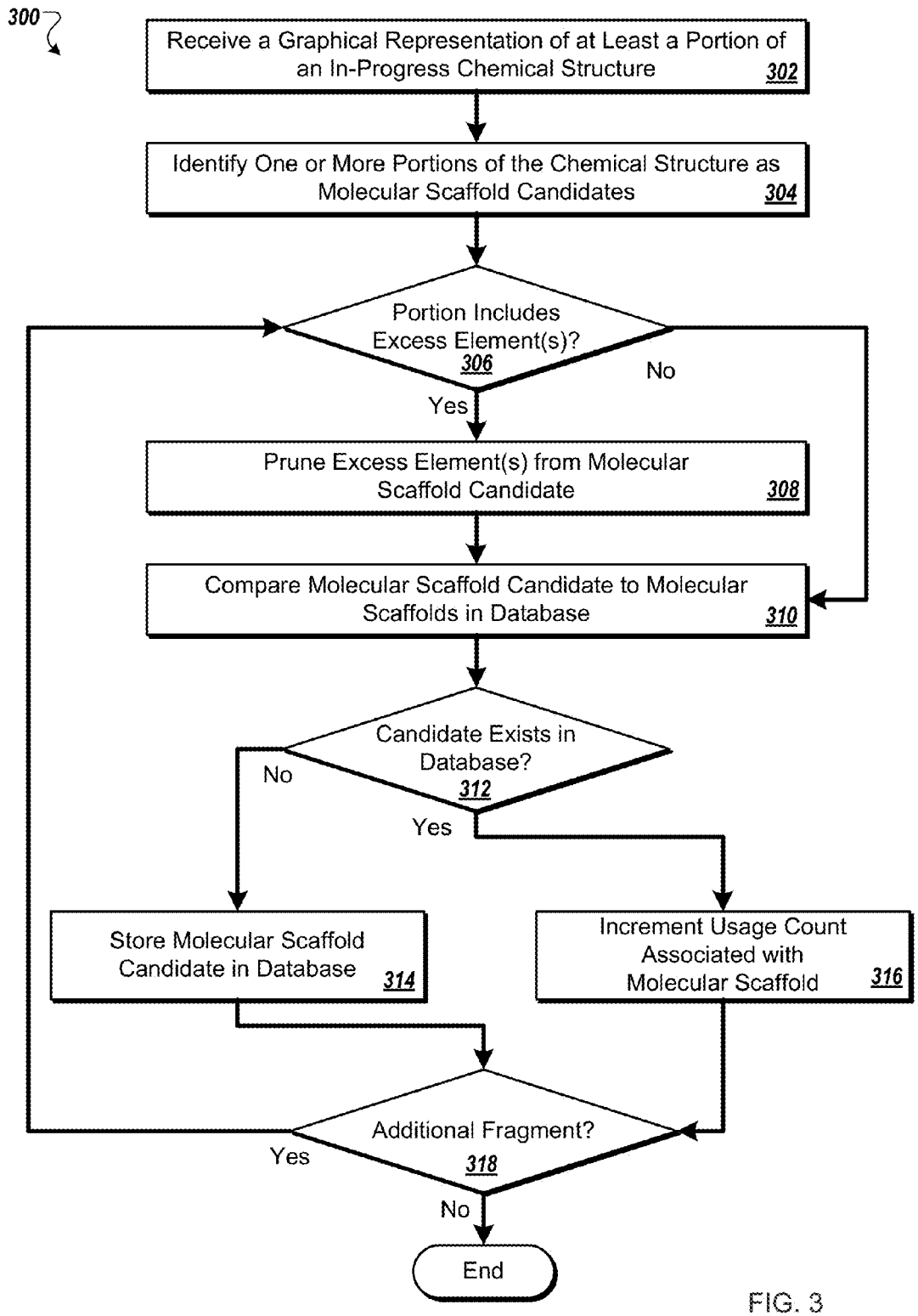
FIG. 3 is a flow chart of an example method for identifying and storing molecular scaffolds for use in a draw-ahead functionality of a utility for graphical representation of a chemical structure.

FIG. 3 is a flow chart of an example method 300 for identifying and storing molecular scaffolds for use in a draw-ahead utility of a graphical chemical structure editing application. For example, the molecular scaffolds may be identified within prior (or current) drawings created by a particular user or from drawings created by a number of users. In some implementations, the method 300 may be used to mine the drawings created by a number of users accessing a common software license or storing drawings to a common repository (e.g., networked storage device). The method 300, for example, may be used in identifying the first molecular scaffold 202 and the second molecular scaffold 204, shown in FIGS. 2A and 2B.

In some implementations, the method 300 begins with receiving a graphical representation of at least a portion of a chemical structure (302). The graphical representation, in some examples, may include a chemical structure drawing-in-progress, a complete graphical representation of a chemical structure, a graphical representation of a chemical structure imported from a separate software application, or a graphical chemical structure representation stored within a document repository.

In some implementations, one or more portions of the chemical structure are identified as molecular scaffold candidates (304). In some implementations, a molecular scaffold may include a minimum number of elements (e.g., chemical features) such as, for example, at least two hydrocarbon rings. A molecular scaffold, in some implementations, is composed of atoms, hydrocarbon rings, chains, bonds, and/or substituents. In some implementations, a molecular scaffold may be identified by receiving a molecular structure as a "favorite" from a user, for example, through a user interface capture feature. For example, a user may enter or select one or more molecular scaffolds that the user anticipates drawing frequently.

In some implementations, a collection of molecular structures are received and reviewed to identify molecular scaffold candidates. For example, molecular structures may be captured in a registration system (e.g., registering molecules to associate with a software license or user identification within a system including a chemical formula drawing program with draw-ahead feature), culled from public data sets, read from a small molecule database such as the Available Chemicals Exchange (ACX) maintained by PerkinElmer of Waltham, Mass., captured as new molecules from an electronic lab notebook (ELN) system, or identified through optical character recognition (OCR) systems.

In reviewing a collection of molecular structures (e.g. as obtained from one or more of the avenues identified above), in some implementations, a routine is used to identify one or more maximum common substructures among the collection (e.g., appearing two or more times, etc.). In some implementations, a routine iteratively identifies common substructures within the collection. The routine, for example, may identify common substructures including at least a threshold number of elements (e.g., chemical features such as atoms, hydrocarbon rings, chains, bonds, and/or substituents), as described above. The routine may identify the largest common substructure among a collection of molecules.

If a potential molecular scaffold candidate includes one or more excess elements (306), in some implementations, the portion may be pruned to determine a molecular scaffold candidate (308). For example, as illustrated within FIG. 2B, the bond 112i, not being directly connected to a particular hydrocarbon ring, may be pruned away. In other words, in this example, elements not belonging to hydrocarbon rings are eligible for pruning. In some implementations, superatoms (e.g., CBZ, COOH, etc.) may be pruned when identifying a molecular scaffold candidate. In other examples, bond order simplification and/or atom simplification methods may be applied, such as replacing all bonds with single bonds, removing stereochemistry, and reducing the molecular scaffold candidate to an exemplar element (e.g., making all heavy atoms C). If the molecular structure candidate was identified in a set of molecular structures obtained from a database, in one example, unnatural fragments may be removed. For example, salt stripping may be applied.

In some implementations, the molecular scaffold candidate is compared to molecular scaffolds in a database of molecular scaffolds (310). In some implementations, a chemical structure creation and editing application includes a database of common molecular scaffolds. For example, upon installing the application, a draw-ahead feature may have access to a database of common molecular scaffolds for presentation as draw-ahead options. The database of molecular scaffolds, in some implementations, contains one or more molecular scaffolds identified as portions of other graphical representations of chemical structures. For example, the method 300 may have been performed previously on a chemical structure to derive one or more molecular scaffolds.

In some implementations, a sub-structure of a molecular candidate may be compared to a sub-structure of a molecular structure within the database. For example, as illustrated in FIGS. 2A and 2B, the first molecular scaffold 202 may be compared to a first portion of the candidate molecular scaffold. Features of the candidate such as, in some examples, the number and placement of atoms, the number and placement of bonds, the order of each bond (e.g., double, single, triple), stereochemistry, formal or partial charge, or cis/trans isomerism (e.g., bond orientations) may be compared to one or more molecular scaffolds in the database to identify a match.

If a match of the candidate molecular scaffold is identified within the database (312), in some implementations, a usage count associated with the identified molecular scaffold is incremented (316). For example, to track a relative popularity of a particular molecular scaffold, in some implementations, the number of times the particular molecular scaffold has been identified in a graphical representation of a chemical structure may be tracked. In some implementations, the usage count identifies, in part, the number of times a particular molecular scaffold has been selected when presented as a draw-ahead candidate by a draw-ahead feature.

If, instead, a match is not found in relation to the molecular scaffold candidate, in some implementations, the molecular scaffold candidate is stored in the database (314). In some implementations, a foundational portion of the molecular scaffold candidate may be identified such that, in response to matching the foundational portion with a portion of a graphical representation of a chemical structure, the remainder of the molecular scaffold may be offered as a molecular scaffold candidate for draw-ahead purposes. For example, a first two or more atoms, as well as a first bond between two of the first two or more atoms, may be identified as a foundational portion of the molecular scaffold. In some implementations, the method 300 repeats the pruning and comparison steps for the remaining molecular scaffold candidates (318).

Although the method 300 has been described in relation to a series of steps performed in an example order, in other implementations, one or more of the steps of the method 300 may be performed in a different order and/or in parallel, and one or more steps may be added to the method 300. Furthermore, one or more of the steps of the method 300, in other implementations, may be combined or removed. For example, in some implementations, two or more previously iterated molecular scaffold candidates may be combined as a "super-fragment", where the "super fragment" may be compared to the molecular scaffolds identified by the database. In another example, in some implementations, each molecular scaffold may be associated with one or more users (e.g., user identifiers associated with drawings containing the particular molecular scaffold. For example, should user "Bob" commonly draw molecular scaffold A, a usage count associated with both molecular scaffold A and user Bob may be incremented, such that molecular scaffold A will be promoted in priority in relation to other molecular structure candidates when identifying two or more draw-ahead options for Bob. Further to the example, user "Gary," who has never used molecular scaffold A (although it has been used repeatedly by Bob), may be offered a different molecular scaffold as a primary candidate for draw-ahead purposes (e.g., a molecular scaffold previously used by Gary) even when drawing a same chemical structure. Other modifications of the method 300 are possible without straying from the intent and purpose of the method 300.

Figures 4A, 4B:
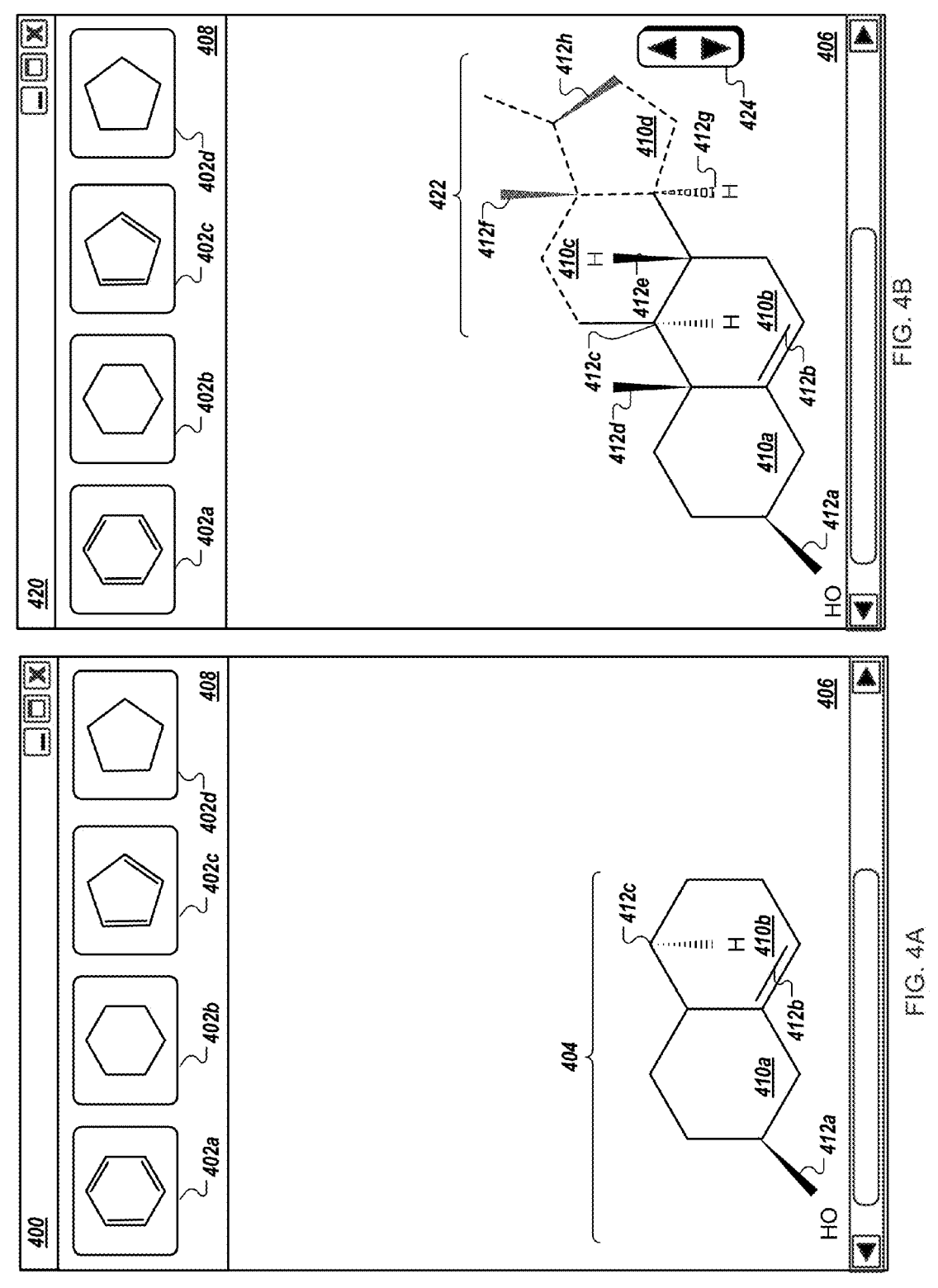

FIGS. 4A and 4B illustrate example screen shots depicting a candidate molecular scaffold 422 being presented to a user as a draw-ahead option based upon a portion 404 of a graphical representation of a chemical structure. The draw-ahead option, for example, may have been previously identified within a different graphical representation of a chemical structure, for example as described by the method 300 illustrated in FIG. 3.

Turning to FIG. 4A, in a first screen shot 400, a user is working on a graphical representation of a chemical structure, currently containing the portion 404 including a set of atoms 410a and 410b as well as bonds 412a, 412b, and 412c. In some implementations, the user constructed the portion 404 using a set of editing tools 402, as illustrated within a tool menu 408. For example, a user may select a particular editing tool 402 from the menu, then select a location in an editing pane 406 for positioning of the selected editing tool feature. In another example, the user may drag and drop a particular editing tool feature 402 into the editing pane 406. Upon each addition of an element of the graphical representation of the chemical structure, in some implementations, a draw-ahead utility invokes a matching function to identify one or more candidate molecular scaffolds to present in relation to the existing portion 404 of a chemical structure. An example of a method for identifying a candidate molecular scaffold based upon a portion of a graphical representation of a chemical structure is described in relation to FIG. 5.

Turning to FIG. 4B, in a second screen shot 420, the candidate molecular scaffold 422 is illustrated as an extension of the existing portion 404. In some implementations, the candidate molecular scaffold 422 is visually rendered in a manner that differentiates the atoms and bonds of the candidate molecular scaffold 422 from the atoms and bonds of the existing portion 404. For example, as illustrated, the candidate molecular scaffold 422 is rendered in part using dashed lines. In other examples, the candidate molecular scaffold 422 may be rendered as a semi-opaque image, in a different color, partially removed from the existing portion 404 (e.g., like a puzzle piece that could be pulled into position), highlighted, outlined, and/or filled in a different color. In some implementations, a second (e.g., preview) pane may pop-up, overlay, or be rendered within the editing pane 406, where the preview pane may illustrate the addition of the candidate molecular scaffold 422 to the existing portion 404.

As illustrated, to match the candidate molecular scaffold 422 with the existing portion 404, bonds 412d and 412e have been added to the existing portion 404. In some implementations, based upon a partial match of an existing portion of a graphical representation of a chemical structure, one or more elements may be added to the existing portion during presentation of a candidate molecular structure.

Next to the candidate molecular scaffold 422, as illustrated in FIG. 4B, a selection control 424, when selected, may present additional candidate molecular scaffolds. For example, by toggling up or down using the directional arrows of the selection control 424, the user may be presented with one or more additional candidate molecular scaffolds. In some implementations, activation of the selection control 424 causes the replacement of the candidate molecular scaffold 422 (and, optionally, any elements added to the existing portion 404 to match the candidate molecular scaffold 422 to the existing portion 404) with a second candidate molecular scaffold (and, optionally, any new elements that may be added to the existing portion 404 to match the second candidate molecular scaffold to the existing portion 404). In other implementations, activation of the selection control 424 may launch a preview window of candidate molecular structures, such that a user may scroll through and select a particular candidate molecular structure for presentation in relation to the existing portion 404. Although illustrated as a bi-directional toggle control, other controls are possible.

Additionally, in some implementations, a natural language interface may be used provide input to the selection of candidate molecular scaffolds. For example, the terms "next" and "back", when uttered, may cause the user interface to scroll through molecular scaffold candidates.

Once a candidate molecular scaffold has been decided upon, in some implementations, the selection control 424 is removed from the editing pane and the candidate molecular scaffold is presented in the same drawing style (e.g., color, line width, transparency, background, etc.) as the existing portion 404. In some implementations, a user may select the presented candidate molecular scaffold 422 (e.g., touching, clicking, mousing over while activating an enter key, etc.) to indicate acceptance of the candidate molecular scaffold 422. In other implementations (not illustrated), a portion of the selection control 424 or a separate control may be used to indicate acceptance of the candidate molecular scaffold 422. In implementations involving a natural language interface, for example, a term such as "select" or "add", when uttered, may indicate acceptance of an active (e.g., currently presented) candidate molecular scaffold.

Figure 5:
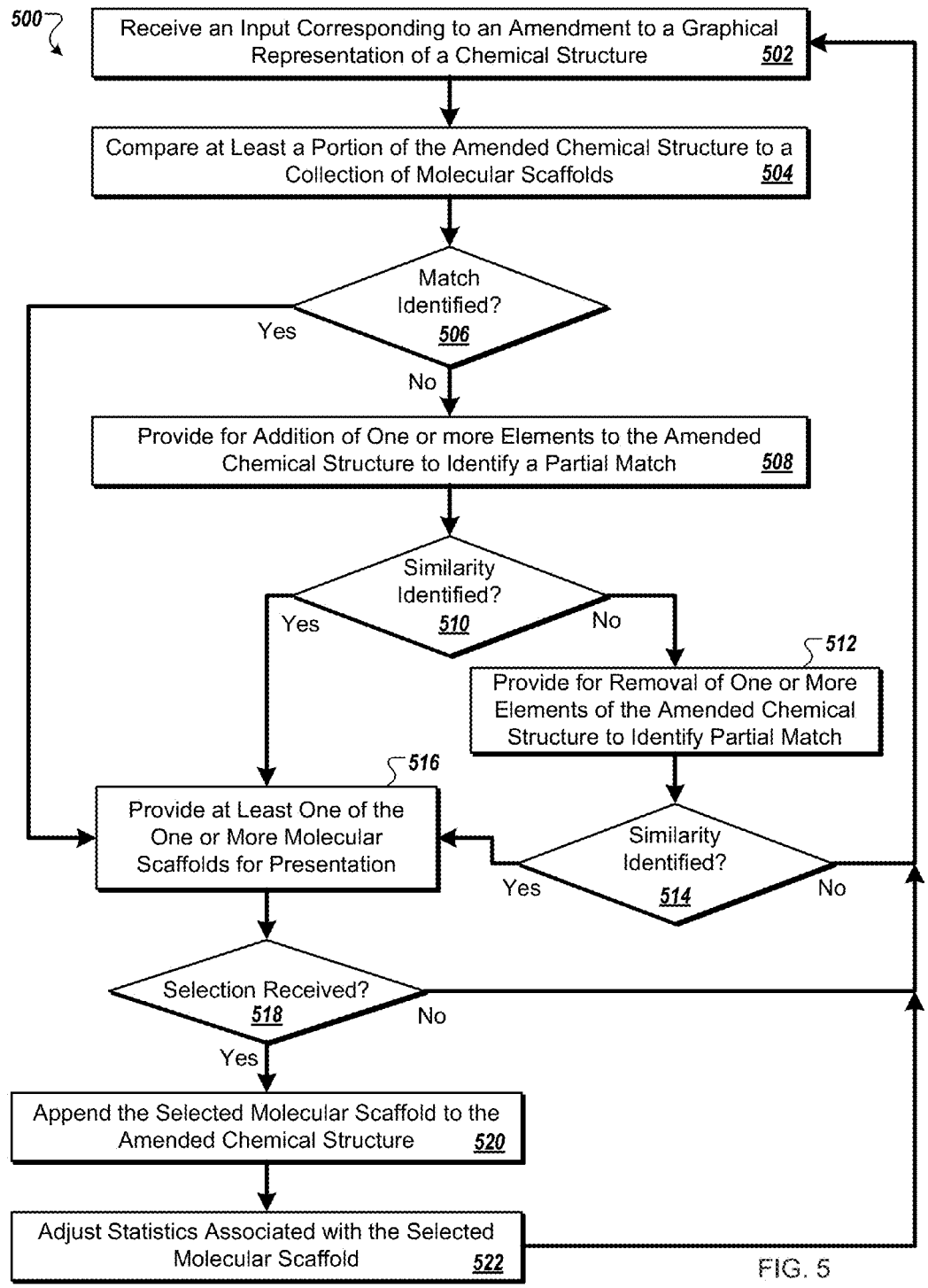
FIG. 5 is a flow chart of an example method for identifying and presenting candidate molecular scaffolds in a draw-ahead functionality of a utility for graphical representation of a chemical structure.

FIG. 5 is a flow chart of an example method 500 for identifying and presenting candidate molecular scaffolds in a draw-ahead functionality of a utility for graphical representation of a chemical structure. The method 500, in some implementations, may be used to identify and present one or more candidate molecular scaffolds based upon an existing portion of a graphical representation of a chemical structure. As illustrated in FIGS. 4A and 4B, for example, the method 500 may review the existing portion 404 and offer the candidate molecular scaffold 422 as an option for continuing the drawing of the graphical representation of a chemical structure.

The method 500, in some implementations, begins with receiving an input corresponding to an amendment to a graphical representation of a chemical structure (502). The graphical representation of a chemical structure, for example, includes one or more atoms, hydrocarbon rings, chains, bonds, and/or substituents. The graphical representation of the chemical structure, for example, may have been developed by a user "from scratch", e.g. through adding elements to a work area of a chemical structure drawing tool. In another example, the graphical representation of the chemical structure may be brought into the chemical structure drawing tool (e.g., selected from a favorites list, opened from a saved file, imported from an electronic lab notebook, etc.). The graphical representation of the chemical structure, in some implementations, includes a portion or a fragment of a molecular structure. A user, interacting with a graphical representation of a chemical structure within a graphical user interface, may make a modification to the graphical representation of the chemical structure such as, in some examples, addition of an atom, addition of a bond, removal of an atom, and/or removal of a bond. In some implementations, the method 500 may only be invoked based upon particular types of amendments. For example, in some examples, the method 500 may be invoked in response to addition of an atom, ring, chain, bond, and/or substituent to a structure having at least a minimum specified size, in response to a user saving a current state of a draft chemical structure, or in response to the addition of a candidate molecular scaffold to the graphical representation of a chemical structure. Also, the method 500 may be invoked in response to the drawing of or selection of a chemical structure fragment of a designated minimum size. As used herein, an "amendment" of a chemical structure representation may include modification of, as well as creation of, a chemical structure representation.

In some implementations, at least a portion of the amended chemical structure is compared to a collection of molecular scaffolds (504). The collection of molecular scaffolds, in some implementations, includes one or more previously drawn chemical structures or portions of chemical structures. In some implementations, the collection of molecular scaffolds includes one or more commonly identified portions of chemical structures, for example as identified through a database of graphical representations of known chemical structures. In a particular example, a collection of graphical representations of known chemical structures, such as the PubChem Compound database maintained by the National Center for Biotechnology Information (NCBI) or the molecular spectral databases maintained by the National Institute of Standards and Technology (NIST), can be harvested to identify commonly reoccurring chemical units as molecular scaffolds. In another example, an entity (e.g., university, corporation, research organization, etc.) may populate the database of molecular scaffolds with one or more molecular scaffolds (e.g., imported from graphical representations of chemical structures previously constructed by the entity). The molecular scaffolds, in some implementations, are categorized and stored in a database for querying based upon a partial match (e.g., a match of two or more atoms and two or more bonds between the reoccurring chemical unit and a portion of a graphical representation of a chemical structure.

The portion of the amended chemical structure to be compared to the collection of molecular scaffolds may be identified using various methods. For example, the utility may identify the location of the user's edit of the molecule. Then, the utility may look in the immediate locale to find fragments (molecular scaffolds) in the database that have a substructure in common with this locale. The search may be biased by molecular scaffolds that are drawn more often or more frequently than others.

Thus, in some implementations, common chemical structure fragments identified within the collection of molecular scaffolds may be used to provide guidelines on how to break down an amended chemical structure into one or more portions for purposes of identifying a matching molecular scaffold from the collection. For example, frequently occurring sub-structures of the molecular scaffolds in the collection may be identified, and these frequently occurring sub-structures may be used as a basis for breaking down a graphical representation of a chemical structure into a series of portions, or fragments. In some implementations, a modified section of the chemical structure, such as two or more hydrocarbon rings and/or their substituents in closest proximity to the point of amendment, is compared to the collection of molecular scaffolds. For example, the portion may be selected to contain at least a threshold number of elements, such as at least two hydrocarbon rings.

In some implementations, a portion (up to all) of the amended chemical structure in the vicinity of the amendment is compared to a sub-structure, such as a designated connection structure, of a molecular scaffold from the collection. For example, referring to FIGS. 4A and 4B, upon amendment, the portion 404 may be compared to the rings 410$a$ and 410$b$ as well as bonds/substituents 412$a$ through 412$e$, where the combination of the rings 410$a$ and 410$b$ and the bond/substituents 412$a$ through 412$e$ is a sub-structure of a molecular scaffold including both a sub-structure matching the portion 404 and a sub-structure containing the candidate molecular scaffold 422.

If a match between the portion of the amended chemical structure and a molecular scaffold from the collection is not found (506), in some implementations, a provision is made for the addition of one or more elements to the amended chemical structure to identify a partial match (508). Returning to the example above, consider that the molecular scaffold includes a sub-structure identified by the portion 404 plus the bonds 412$d$ and 412$e$, and the molecular scaffold is being compared to the portion 404 (e.g., without the bonds 412$d$ and 412$e$). In some implementations, a partial match may be determined, based upon the placement of one or more additional elements to generate a positive match. For example, the method may assume that the user has not yet added the bonds 412$d$ and 412$e$ but this addition is a likely intention.

If a similarity is not identified between the portion of the amended chemical structure and one or more molecular scaffolds (510), in some implementations, a provision is made for removal of one or more elements of the amended chemical structure to identify a partial match (512). Turning again to FIGS. 4A and 4B, consider a molecular scaffold matching the portion of a chemical structure including rings 410$a$ through 410$d$ and bonds/substituents 412$b$ through 412$h$, but lacking the bond 412$a$. In some implementations, an existing portion of a chemical structure may be logically "pruned" to identify a partial match.

In some implementations, a molecular candidate may be identified based upon chemical similarity, e.g., as represented by a chemical structure similarity measure such as a tanimoto score. For example, a particular molecular candidate may be represented as a first set of keys (e.g., Elsevier MDL structural keys, etc.) and the first molecular scaffold 202 may be represented as a second set of keys. A similarity match may be conducted by determining a distance (e.g., similarity) between the two sets of keys.

If no matches or similarities are located (514), in some implementations, the method 500 returns to waiting to receive an input corresponding to an amendment to the graphical representation of the chemical structure (502). Then, based upon further input, such as addition or removal of another atom, ring, chain, bond, and/or substituent to or from the graphical representation of the chemical structure, the method 500 may locate a candidate molecular scaffold for appending to or otherwise modifying the graphical representation of the chemical structure.

Conversely, if any match or similarity is located, in some implementations, the matching and/or similar molecular scaffolds are provided for presentation within a graphical user interface (516). For example, the potential match may be presented as a selectable amendment in any of the manners described in relation to FIG. 4B.

If a selection of a particular molecular scaffold of the one or more molecular scaffolds is not received (518), in some implementations, the method 500 returns to waiting to receive an input corresponding to an amendment to the graphical representation of the chemical structure (502).

If, instead, selection of a particular molecular scaffold of the one or more molecular scaffolds is received (518), in some implementations, the selected molecular scaffold is appended to the amended chemical structure (520), or the in-progress chemical structure is replaced or partially replaced with the selected molecular scaffold, as appropriate. Appending the molecular scaffold, for example, can include causing the re-generation of a graphical user interface to include the portion of the molecular scaffold previously presented as an option to the user.

In some implementations, statistics associated with the selected molecular scaffold are adjusted (522). To determine an order in which to present multiple molecular scaffold candidates to a user, the method 500 may adjust one or more statistics related to a selected molecular scaffold. In some examples, the statistics may include a usage count, a timestamp, and a list of users who have selected the particular molecular scaffold. The statistics may be gathered related to the molecular scaffold in general and/or a per user basis. For example, a first user may more commonly draw a first set of molecular scaffolds, while a second user may more commonly draw a second set of molecular scaffolds. In some implementations, molecular scaffolds are collected as sub-portions, and statistics may be stored regarding particular combinations of sub-portions. For example, the method 500 may track the number of times the combination of the portion 404 without the bond 412a is used in combination with the portion 422, in comparison to the number of times the combination of the portion 404 in whole is used in combination with the portion 422. In some implementations, statistics may be collected related to the frequency in which two molecular scaffolds appear in a same graphical representation of a chemical structure. For example, it may be determined that users who select (or draw) molecular scaffold Y are very likely to later select (or draw) molecular scaffold Z. Other statistics are possible.

Upon receipt of an additional amendment to the graphical representation of the chemical structure (502), in some implementations, the method 500 may repeat.

Although the method 500 has been described in relation to a series of steps performed in an example order, in other implementations, one or more of the steps of the method 500 may be performed in a different order and/or in parallel, and one or more steps may be added to the method 500. For example, rather than providing one or more molecular scaffolds for presentation (516) after having only identified one or two matches (506), in some implementations, the method 500 may continue to attempt to identify similarities (e.g., as described in relation to steps 508 through 514) until a threshold number of matches (e.g., three, five, etc.) has been identified. Conversely, should identification of the one or more molecular scaffolds (506) produce greater than a threshold number of molecular scaffold candidates (e.g., five, ten, twenty, etc.), in some implementations, the method 500 prioritizes the matching molecular scaffolds in a ranked order and only provides the top N matches for presentation to the user (516). In other implementations, should identification of the one or more molecular scaffolds (506) produce greater than a threshold number of molecular scaffold candidates, the method 500 returns to waiting to receiving an additional amendment (502). For example, rather than overwhelm a user with constant options for molecular scaffold candidates, the method 500 may wait to present molecular scaffold candidates that may, presumably, have a higher chance of being desirable to the user. Prior to providing at least one of the one or more molecular scaffolds for presentation (516), in some implementations, the candidate molecular scaffolds may be ranked in order of priority (e.g., according to one or more statistical values associated with the molecular scaffolds and/or according to whether a particular molecular scaffold was a direct match or a similar match).

Furthermore, one or more of the steps of the method 500, in other implementations, may be combined or removed. For example, in some implementations, steps 512 and 514 may be removed, causing matches to only be served on the existing portion of the chemical structure. In some implementations, the method 500 may begin with identifying one or more molecular scaffolds for presentation to begin a drawing project of a new visual representation of a chemical structure. In one example, based upon user information (e.g., user preferences, user favorites list, user history, user group membership, etc.), the method 500 may identify one or more molecular scaffold candidates to present to the user as a basis for the new drawing project. Other modifications of the method 500 are possible without straying from the intent and purpose of the method 500.

Figure 6:
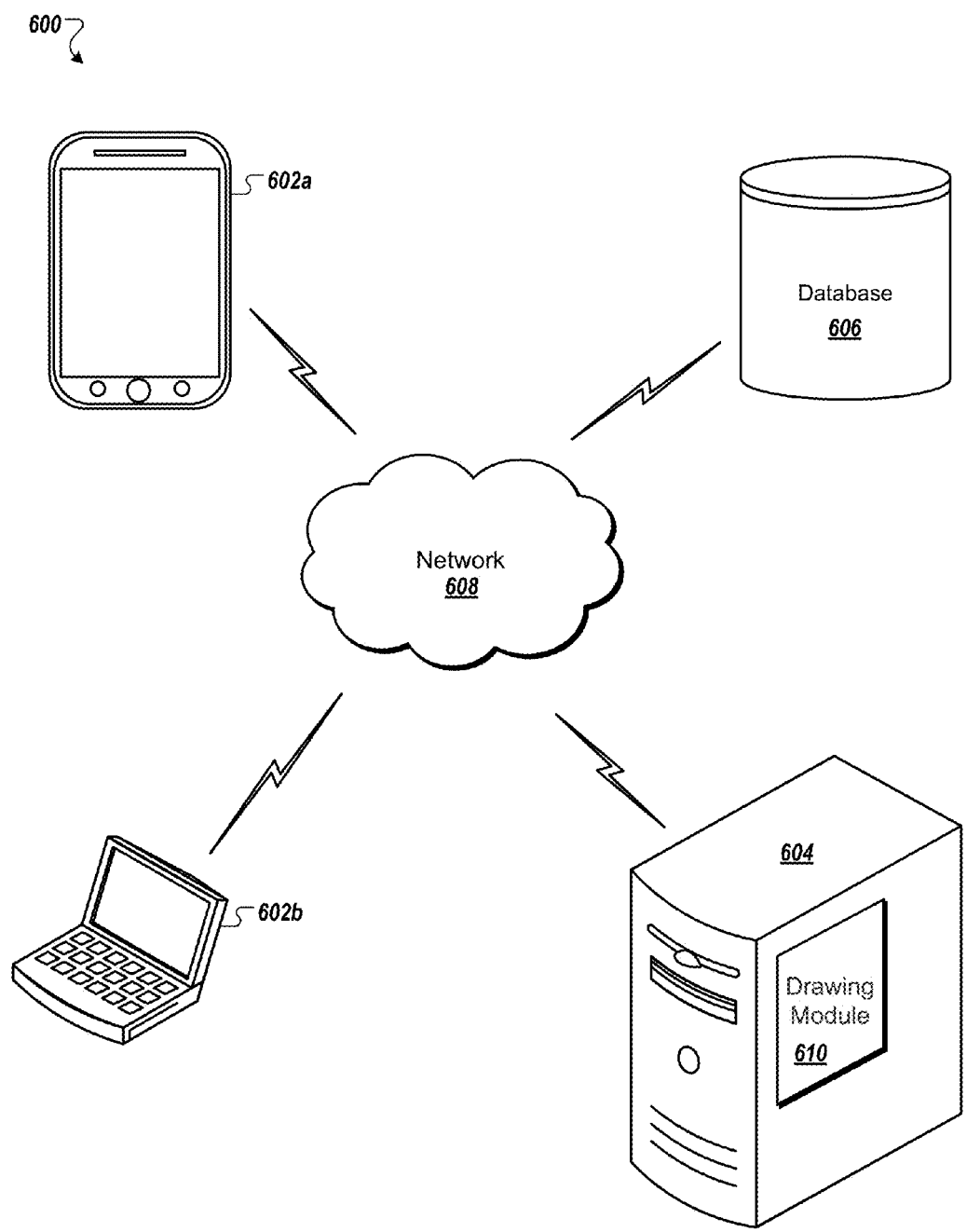
FIG. 6 is a schematic diagram of an example system for drawing or editing chemical structures.

FIG. 6 depicts an example system 600 for drawing or editing graphical representations of chemical structures. The system 600 includes client nodes 602a and 602b, a server node 604, a database 606, and, for enabling communications therebetween, a network 608. As illustrated, the server node 604 may include a drawing module 610.

The network 608 may be, for example, a local-area network (LAN), such as a company or laboratory Intranet, a metropolitan area network (MAN), or a wide area network (WAN), such as the Internet. Each of the client nodes 602, server node 604, and the database 606 may be connected to the network 608 through a variety of connections including, but not limited to, standard telephone lines, LAN or WAN links (e.g., T1, T3, 56 kb, X.25), broadband connections (e.g., ISDN, Frame Relay, ATM), or wireless connections. The connections, moreover, may be established using a variety of communication protocols (e.g., HTTP, TCP/IP, IPX, SPX, NetBIOS, NetBEUI, SMB, Ethernet, ARCNET, Fiber Distributed Data Interface (FDDI), RS232, IEEE 802.11, IEEE 802.11a, IEEE 802.11b, IEEE 802.11g, and direct asynchronous connections).

The client node 602a may be any type of wireless device, information appliance, tablet computer, personal digital assistant, cellular phone, handheld device, or other portable computing device that is capable of both presenting information/data to, and receiving commands from, a user of the client node 602a (e.g., an analytical chemist). Similarly, the client node 602b may be any type of personal computer, Windows-based terminal, network computer, wireless device, information appliance, RISC Power PC, X-device, workstation, mini computer, main frame computer, set top box, or other computing device that is capable of both presenting information/data to, and receiving commands from, a user of the client node 602b. The client nodes 602 may include, for example, a graphical display device (e.g., a touch screen or a computer monitor), a data entry device (e.g., a keyboard, a touch screen, or a mouse pad), persistent and/or volatile storage (e.g., computer memory), and a processor. In one embodiment, the client node 602 includes a web browser, such as, for example, Internet Explorer® developed by Microsoft Corporation of Redmond, Wash., to connect to the World Wide Web.

For its part, the server node 604 may be any computing device that is capable of receiving information/data from and delivering information/data to the client nodes 602, for example over the network 608, and that is capable of querying, receiving information/data from, and delivering information/data to the server node 604. For example, as further explained below, the server node 604 may receive input (e.g., a multi-touch gesture) from a user of the client node 602, create or edit a chemical structure representation according to the input, and present or display the chemical structure representation to the user at the client node 602. The server node 604 may include a processor and persistent and/or volatile storage, such as computer memory.

The server node 604 may be any computing device that is capable of storing and managing collections of data, such as data relating to chemical structure representations. The chemical structure representations may be, for example, of the type described in related U.S. patent application Ser. No. 13/100,217, filed May 3, 2011, titled "Systems, Methods, and Apparatus for Processing Documents to Identify Structures," and related U.S. application Ser. No. 13/239,069, filed, Sep. 21, 2011, titled "Systems, Methods, and Apparatus for Facilitating Chemical Analyses," and related International Patent Application No. PCT/US12/26574, filed Feb. 24, 2012, titled "Systems, Methods, and Apparatus for Drawing Chemical Structures Using Touch and Gestures," the disclosures of each of which are hereby incorporated by reference herein in their entireties.

As used herein, the term "server node" is broadly used to refer to any repository of information. The data stored within the server node 604 may be harvested from the server node 604 in any manner. In one embodiment, the harvesting is performed utilizing indexing and structure recognition algorithms, and the harvested data is connected together by examining and correlating the disjointed information that is found.

The drawing module 610 of the server node 604 may be implemented as any software program and/or hardware device, for example an application specific integrated circuit (ASIC) or a field programmable gate array (FPGA), that is capable of providing the functionality described herein. It will be understood by one having ordinary skill in the art, however, that the illustrated module 610, and the organization of the server node 604, are conceptual, rather than explicit, requirements. For example, it should be understood that the drawing module 610 may in fact be implemented as multiple modules, such that the functions performed by the single module, as described herein, are in fact performed by the multiple modules.

Although not shown in FIG. 6, any or all of the client nodes 602, the server node 604, and the database 606 may also include its own transceiver (or separate receiver and transmitter) that is capable of receiving and transmitting communications, including requests, responses, and commands, such as, for example, inter-processor communications and networked communications. The transceivers (or separate receivers and transmitters) may each be implemented as a hardware device, or as a software module with a hardware interface.

It will also be understood by those skilled in the art that FIG. 6 is a simplified illustration of the system 600 and that it is depicted as such to facilitate the explanation of various embodiments of the present disclosure. Moreover, the system 600 may be modified in a variety of manners without departing from the spirit and scope of the present disclosure. For example, rather than being implemented on a single server node 604, the drawing module 610 may instead be implemented on a different computing device (not shown) and such computing devices may communicate with one another directly, over the network 608, or over another additional network (not shown). In yet another example, the functionality of the server node 604 may in fact be resident on the server node 604 (e.g., be implemented in the computer memory thereof). Additional options are for the server node 604 and/or the database 606 to be local to the client node 602 (such that they may all communicate directly without using the network 608), or for the functionality of the server node 604 and/or the database 606 to be implemented on the client node 602 (e.g., for the drawing module 610 and/or the server node 604 to reside on the client node 602). As such, the depiction of the system 600 in FIG. 6 is non-limiting.

In certain embodiments, the system 600 allows a user to draw and edit a chemical structure representation using one or more fingers on an input interface, such as a touch pad or touch screen, at the client tablet node 602a. The system 600, in some embodiments, allows a user to draw and edit a graphical representation of a chemical structure using a mouse, stylus, keypad, trackball, or other input interface, such as an input interface at a client personal computer 602b. The input interface, in some implementations, may include a natural language processing module capable of converting utterances to a series of commands for activating controls of the user interface.

In general, the drawing module 610 in the server node 604 is configured to draw or revise the chemical structure representation according to the input from the user, as explained above with respect to the prior figures. The drawing module 610 may then provide an image (e.g., a collection of pixels) of the graphical representation of the chemical structure for presentation to the user on the graphical display of the particular client node 602. Additionally, the drawing module 610 may present one or more candidate molecular scaffolds for amendment to a graphical representation of a chemical structure. The candidate molecular scaffolds, for example, may be identified from molecular scaffolds stored within the database 606. In general, the system 600 may be used to perform any of the methods described herein.

Figure 7:
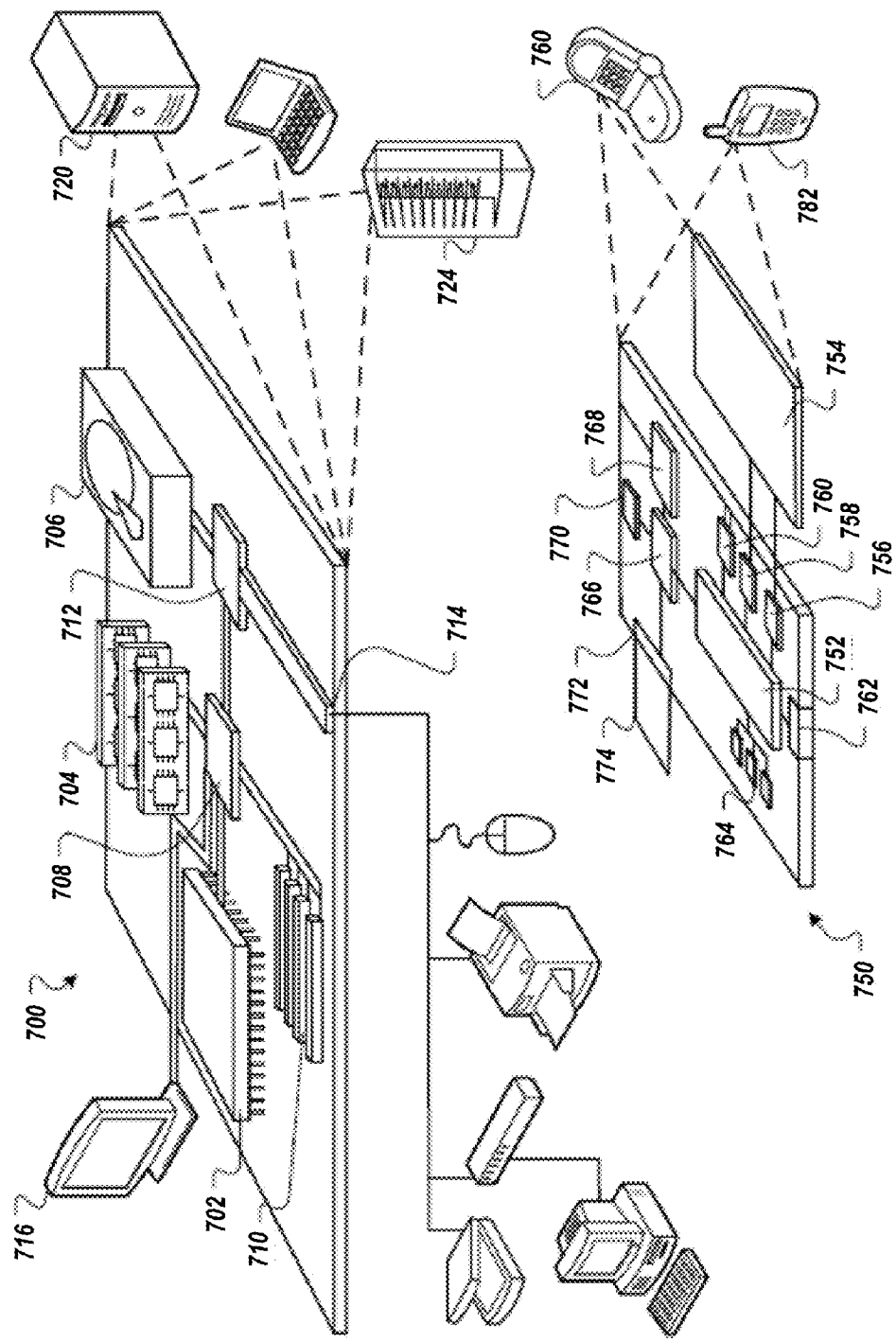
FIG. 7 is a block diagram of an example computing device and an example mobile computing device.

FIG. 7 shows an example of a computing device 700 and a mobile computing device 750 that can be used to implement the techniques described in this disclosure. The computing device 700 is intended to represent various forms of digital computers, such as laptops, desktops, workstations, personal digital assistants, servers, blade servers, mainframes, and other appropriate computers. The mobile computing device 750 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 700 includes a processor 702, a memory 704, a storage device 706, a high-speed interface 708 connecting to the memory 704 and multiple high-speed expansion ports 710, and a low-speed interface 712 connecting to a low-speed expansion port 714 and the storage device 706. Each of the processor 702, the memory 704, the storage device 706, the high-speed interface 708, the high-speed expansion ports 710, and the low-speed interface 712, are interconnected using various busses, and may be mounted on a common motherboard or in other manners as appropriate. The processor 702 can process instructions for execution within the computing device 700, including instructions stored in the memory 704 or on the storage device 706 to display graphical information for a GUI on an external input/output device, such as a display 716 coupled to the high-speed interface 708. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 704 stores information within the computing device 700. In some implementations, the memory 704 is a volatile memory unit or units. In some implementations, the memory 704 is a non-volatile memory unit or units. The memory 704 may also be another form of computer-readable medium, such as a magnetic or optical disk.

The storage device 706 is capable of providing mass storage for the computing device 700. In some implementations, the storage device 706 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 702), perform one or more methods, such as those described above. The instructions can also be stored by one or more storage devices such as computer- or machine-readable mediums (for example, the memory 704, the storage device 706, or memory on the processor 702).

The high-speed interface 708 manages bandwidth-intensive operations for the computing device 700, while the low-speed interface 712 manages lower bandwidth-intensive operations. Such allocation of functions is an example only. In some implementations, the high-speed interface 708 is coupled to the memory 704, the display 716 (e.g., through a graphics processor or accelerator), and to the high-speed expansion ports 710, which may accept various expansion cards (not shown). In the implementation, the low-speed interface 712 is coupled to the storage device 706 and the low-speed expansion port 714. The low-speed expansion port 714, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 720, or multiple times in a group of such servers. In addition, it may be implemented in a personal computer such as a laptop computer 722. It may also be implemented as part of a rack server system 724. Alternatively, components from the computing device 700 may be combined with other components in a mobile device (not shown), such as a mobile computing device 750. Each of such devices may contain one or more of the computing device 700 and the mobile computing device 750, and an entire system may be made up of multiple computing devices communicating with each other.

The mobile computing device 750 includes a processor 752, a memory 764, an input/output device such as a display 754, a communication interface 766, and a transceiver 768, among other components. The mobile computing device 750 may also be provided with a storage device, such as a micro-drive or other device, to provide additional storage. Each of the processor 752, the memory 764, the display 754, the communication interface 766, and the transceiver 768, are interconnected using various buses, and several of the components may be mounted on a common motherboard or in other manners as appropriate.

The processor 752 can execute instructions within the mobile computing device 750, including instructions stored in the memory 764. The processor 752 may be implemented as a chipset of chips that include separate and multiple analog and digital processors. The processor 752 may provide, for example, for coordination of the other components of the mobile computing device 750, such as control of user interfaces, applications run by the mobile computing device 750, and wireless communication by the mobile computing device 750.

The processor 752 may communicate with a user through a control interface 758 and a display interface 756 coupled to the display 754. The display 754 may be, for example, a TFT (Thin-Film-Transistor Liquid Crystal Display) display or an OLED (Organic Light Emitting Diode) display, or other appropriate display technology. The display interface 756 may comprise appropriate circuitry for driving the display 754 to present graphical and other information to a user. The control interface 758 may receive commands from a user and convert them for submission to the processor 752. In addition, an external interface 762 may provide communication with the processor 752, so as to enable near area communication of the mobile computing device 750 with other devices. The external interface 762 may provide, for example, for wired communication in some implementations, or for wireless communication in other implementations, and multiple interfaces may also be used.

The memory 764 stores information within the mobile computing device 750. The memory 764 can be implemented as one or more of a computer-readable medium or media, a volatile memory unit or units, or a non-volatile memory unit or units. An expansion memory 774 may also be provided and connected to the mobile computing device 750 through an expansion interface 772, which may include, for example, a SIMM (Single In Line Memory Module) card interface. The expansion memory 774 may provide extra storage space for the mobile computing device 750, or may also store applications or other information for the mobile computing device 750. Specifically, the expansion memory 774 may include instructions to carry out or supplement the processes described above, and may include secure information also. Thus, for example, the expansion memory 774 may be provide as a security module for the mobile computing device 750, and may be programmed with instructions that permit secure use of the mobile computing device 750. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 752), perform one or more methods, such as those described above. The instructions can also be stored by one or more storage devices, such as one or more computer- or machine-readable mediums (for example, the memory 764, the expansion memory 774, or memory on the processor 752). In some implementations, the instructions can be received in a propagated signal, for example, over the transceiver 768 or the external interface 762.

The mobile computing device 750 may communicate wirelessly through the communication interface 766, which may include digital signal processing circuitry where necessary. The communication interface 766 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 768 using a radio-frequency. In addition, short-range communication may occur, such as using a Bluetooth®, Wi-Fi™, or other such transceiver (not shown). In addition, a GPS (Global Positioning System) receiver module 770 may provide additional navigation- and location-related wireless data to the mobile computing device 750, which may be used as appropriate by applications running on the mobile computing device 750.

The mobile computing device 750 may also communicate audibly using an audio codec 760, which may receive spoken information from a user and convert it to usable digital information. The audio codec 760 may likewise generate audible sound for a user, such as through a speaker, e.g., in a handset of the mobile computing device 750. Such sound may include sound from voice telephone calls, may include recorded sound (e.g., voice messages, music files, etc.) and may also include sound generated by applications operating on the mobile computing device 750.

The mobile computing device 750 may be implemented in a number of different forms, as shown in the figure. For example, it may be implemented as a cellular telephone 780. It may also be implemented as part of a smart-phone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

It should also be noted that embodiments of the present disclosure may be provided as one or more computer-readable programs embodied on or in one or more articles of manufacture. The article of manufacture may be any suitable hardware apparatus, such as, for example, a floppy disk, a hard disk, a CD ROM, a CD-RW, a CD-R, a DVD ROM, a DVD-RW, a DVD-R, a flash memory card, a PROM, a RAM, a ROM, or a magnetic tape. In general, the computer-readable programs may be implemented in any programming language. Some examples of languages that may be used include C, C++, or Java. The software programs may be further translated into machine language or virtual machine instructions and stored in a program file in that form. The program file may then be stored on or in one or more of the articles of manufacture.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

In view of the structure, functions and apparatus of the systems and methods described here, in some implementations, systems and methods for creating graphical representations of chemical structures using a draw-ahead utility are provided. Having described certain implementations of methods and apparatus for creating graphical representations of chemical structures using a draw-ahead utility, it will now become apparent to one of skill in the art that other implementations incorporating the concepts of the disclosure may be used. Therefore, the disclosure should not be limited to certain implementations, but rather should be limited only by the spirit and scope of the following claims.

The invention claimed is:

1. An apparatus for creating a graphical representation of a chemical structure using a draw-ahead feature, the apparatus comprising:
a memory for storing a set of instructions; and
a processor for executing the set of instructions, wherein the instructions, when executed, cause the processor to:
provide a representation of at least a portion of an in-progress chemical structure for presentation on a graphical display;
receive an input corresponding to an amendment to the portion of the in-progress chemical structure;
identify a review portion of the amended in-progress chemical structure for comparison with a collection of stored molecular scaffolds;
identify, by comparing the review portion to the collection of stored molecular scaffolds, one or more candidate molecular scaffolds, wherein each molecular scaffold of the one or more identified candidate molecular scaffolds is determined to, upon one or both of (i) appending to the review portion of the in-progress chemical structure and (ii) replacing or partially replacing the review portion of the in-progress chemical structure, provide at least a portion of a molecular scaffold from the collection of molecular scaffolds, wherein identifying the one or more candidate molecular scaffolds comprises:
identifying one or more matching molecular scaffolds from the collection of molecular scaffolds by determining the review portion to be a sub-structure of each matching molecular scaffold; and
for each matching molecular scaffold, identifying one or more respective candidate molecular scaffolds, wherein each of the one or more respective candidate molecular scaffolds is a sub-structure of the matching molecular scaffold distinct from the review portion;
provide the one or more identified candidate molecular scaffolds for presentation on the graphical display as option(s) for selection by a user in creating the graphical representation of the chemical structure, wherein providing the one or more candidate molecular scaffolds for presentation on the graphical display comprises visually rendering at least one of the candidate molecular scaffolds as an extension of the in-progress chemical structure;
receive an indication of user selection of a selected molecular scaffold of the one or more identified candidate molecular scaffolds provided; and
append the selected molecular scaffold to the review portion of the in-progress chemical structure or replace or partially replace the review portion of the in-progress chemical structure with the selected molecular scaffold, thereby updating the representation of the in-progress chemical structure.

2. The apparatus of claim 1, wherein the instructions, when executed, further cause the processor to, prior to providing the one or more candidate molecular scaffolds for presentation, determine that a total number of the one or more candidate molecular scaffolds does not exceed a threshold number of molecular scaffolds.

3. The apparatus of claim 1, wherein the input corresponding to the amendment to the portion of the in-progress chemical structure comprises at least one of addition of an atom, ring, chain, bond, and/or substituent to a structure having at least a minimum specified size.

4. The apparatus of claim 1 wherein the one or more candidate molecular scaffolds comprise one or more commonly used molecular scaffolds.

5. The apparatus of claim 4, wherein the commonly used molecular scaffolds are scaffolds input and/or selected by a user or group of users at least a threshold number of times.

6. The apparatus of claim 1, wherein the one or more identified candidate molecular scaffolds comprise one or more molecular scaffolds selected from an active database of candidate scaffolds.

7. The apparatus of claim 1, wherein the instructions, when executed, cause the processor to arrange the one or more identified candidate molecular scaffolds in a ranked order prior to providing the one or more candidate molecular scaffolds for presentation on the graphical display.

8. The apparatus of claim 7, wherein arranging the one or more candidate molecular scaffolds in the ranked order comprises identifying a usage count associated with each molecular scaffold of the one or more candidate molecular scaffolds.

9. The apparatus of claim 7, wherein arranging the one or more candidate molecular scaffolds in the ranked order comprises matching a user identifier associated with at least one molecular scaffold of the one or more candidate molecular scaffolds to a user identifier associated with the review portion of the chemical structure.

10. The apparatus of claim 1, wherein receiving the input comprises receiving the input, over a network, from a computing device.

11. The apparatus of claim 1, wherein the one or more molecular scaffolds are stored in the memory.

12. The apparatus of claim 1, wherein the one or more molecular scaffolds are stored in a database.

13. The apparatus of claim 1, wherein the instructions, when executed, cause the processor to:
provide the one or more identified candidate molecular scaffolds for presentation on the graphical display as option(s) for selection by a user in creating the graphical representation of the chemical structure,
wherein providing the one or more candidate molecular scaffolds for presentation on the graphical display comprises visually rendering at least one of the candidate molecular scaffolds as an extension of the in-progress chemical structure; and visually rendering said candidate molecular scaffold in a manner that differentiates the identified candidate molecular scaffold from the in-progress chemical structure.

14. The apparatus of claim 13, wherein the instructions, when executed, cause the processor to visually render the identified candidate molecular scaffold as a semi-opaque extension of the in-progress chemical structure.

15. The apparatus of claim 13, wherein the instructions, when executed, cause the processor to visually render the identified candidate molecular scaffold in a different drawing style than the in-progress chemical structure.

16. The apparatus of claim 13, wherein the instructions, when executed, cause the processor to visually render the identified candidate molecular scaffold in one or more ways selected from the group consisting of
(i) using dashed lines,
(ii) using a different color than the in-progress chemical structure,
(iii) using a spatial separation from the in-progress chemical structure,
(iv) highlighting the identified candidate molecular scaffold in a different color than the in-progress chemical structure, (v) outlining the identified candidate molecular scaffold in a different color than the in-progress chemical structure, and (vi) filling in the identified candidate molecular scaffold in a different color than the in-progress chemical structure.

17. The apparatus of claim 13, wherein the instructions, when executed cause the processor to visually render the identified candidate molecular scaffold as partially removed from the in-progress chemical structure.

18. The apparatus of claim 1, wherein the instructions, when executed cause the processor to:
prior to visually rendering at least one of the candidate molecular scaffolds as an extension of the in-progress chemical structure, provide a preview pane; and
visually render at least one of the candidate molecular scaffolds as an extension of the in-progress chemical structure within the preview pane.

19. The apparatus of claim 1, wherein the instructions, when executed, cause the processor to render a graphical control allowing toggling between different candidate molecular scaffolds of the one or more identified candidate molecular scaffolds.

20. The apparatus of claim 19, wherein the instructions, when executed, cause the processor to:
receive an activation of the graphical control; and
responsive to the received activation of the graphical control, replace a current visual rendering of the at least one candidate molecular scaffold with a visual rendering of a second identified candidate molecular scaffold.

21. The apparatus of claim 19, wherein the instructions, when executed, cause the processor to, responsive to the received activation of the graphical control cause presentation of a preview window for presentation of at least one of the candidate molecular scaffolds.

22. The apparatus of claim 19, wherein the graphical control comprises a bi-directional toggle control.

23. The apparatus of claim 1, wherein the collection of molecular scaffolds includes one or more chemical structures that have been previously rendered and/or one or more chemical structure fragments that have been previously rendered.

24. The apparatus of claim 1, wherein the collection of molecular scaffolds includes one or more chemical structures from a database of graphical representations of known chemical structures.

25. A non-transitory computer readable medium having instructions stored thereon that, when executed, cause a processor to:
provide a representation of at least a portion of an in-progress chemical structure for presentation on a graphical display;
receive an input corresponding to an amendment to the portion of the in-progress chemical structure;
identify a review portion of the amended in-progress chemical structure for comparison with a collection of stored molecular scaffolds;
identify, by comparing the review portion to the collection of stored molecular scaffolds, one or more candidate molecular scaffolds, wherein each molecular scaffold of the one or more identified candidate molecular scaffolds is determined to, upon one or both of (i) appending to the review portion of the in-progress chemical structure and (ii) replacing or partially replacing the review portion of the in-progress chemical structure, provide at least a portion of a molecular scaffold from the collection of molecular scaffolds, wherein identifying the one or more candidate molecular scaffolds comprises:
identifying one or more matching molecular scaffolds from the collection of molecular scaffolds by determining the review portion to be a sub-structure of each matching molecular scaffold; and
for each matching molecular scaffold, identifying one or more respective candidate molecular scaffolds, wherein each of the one or more respective candidate molecular scaffolds is a sub-structure of the matching molecular scaffold distinct from the review portion;
provide the one or more identified candidate molecular scaffolds for presentation on the graphical display as option(s) for selection by a user in creating the graphical representation of the chemical structure,
wherein providing the one or more candidate molecular scaffolds for presentation on the graphical display comprises visually rendering at least one of the candidate molecular scaffolds as an extension of the in-progress chemical structure;
receive an indication of user selection of a selected molecular scaffold of the one or more identified candidate molecular scaffolds provided; and
append the selected molecular scaffold to the review portion of the in-progress chemical structure or replace or partially replace the review amended portion of the in-progress chemical structure with the selected molecular scaffold, thereby updating the representation of the in-progress chemical structure.

26. The non-transitory computer readable medium of claim 25, wherein the review portion of the in-progress chemical structure is all of the in-progress chemical structure.

27. A method of creating a graphical representation of a chemical structure using a draw-ahead feature, the method comprising:
providing a representation of at least a portion of an in-progress chemical structure for presentation on a graphical display;
receiving an input corresponding to an amendment to the portion of the in-progress chemical structure;
identifying, by a processor of a computing device, a review portion of the amended in-progress chemical structure for comparison with a collection of stored molecular scaffolds;
identifying, by a processor of a computing device, by comparing the review portion to the collection of stored molecular scaffolds, one or more candidate molecular scaffolds, wherein each molecular scaffold of the one or more identified candidate molecular scaffolds is determined to, upon one or both of (i) appending to the review portion of the in-progress chemical structure and (ii) replacing or partially replacing the review portion of the in-progress chemical structure, provide at least a portion of a molecular scaffold from the collection of molecular scaffolds, wherein identifying the one or more candidate molecular scaffolds comprises:
identifying one or more matching molecular scaffolds from the collection of molecular scaffolds by determining the review portion to be a sub-structure of each matching molecular scaffold; and
for each matching molecular scaffold, identifying one or more respective candidate molecular scaffolds, wherein each of the one or more respective candidate molecular scaffolds is a sub-structure of the matching molecular scaffold distinct from the review portion;
providing the one or more identified candidate molecular scaffolds for presentation on the graphical display as option(s) for selection by a user in creating the graphical representation of the chemical structure,
wherein providing the one or more candidate molecular scaffolds for presentation on the graphical display comprises visually rendering at least one of the candidate molecular scaffolds as an extension of the in-progress chemical structure;
receiving an indication of user selection of a selected molecular scaffold of the one or more identified candidate molecular scaffolds provided; and
appending the selected molecular scaffold to the review portion of the in-progress chemical structure or replace or partially replacing the review portion of the in-progress chemical structure with the selected molecular scaffold, thereby updating the representation of the in-progress chemical structure.

28. The method of claim 27, wherein the user computing device is the computing device.

29. The method of claim 27, wherein the amendment comprises addition of at least one of an atom, hydrocarbon ring, hydrocarbon chain, bond, and/or substituent.

30. The method of claim 27, wherein the amendment comprises removal of at least one of an atom, hydrocarbon ring, hydrocarbon chain, bond, and/or substituent.

31. An apparatus for creating a graphical representation of a chemical structure using a draw-ahead feature, the apparatus comprising:
a memory for storing a set of instructions; and
a processor for executing the set of instructions, wherein the instructions, when executed, cause the processor to:
provide a representation of at least a portion of an in-progress chemical structure for presentation on a graphical display;
receive an input corresponding to an amendment to the portion of the in-progress chemical structure;
determine a point of amendment to the portion of the in-progress chemical structure;
identify a set of common chemical structure fragments corresponding to frequently occurring sub-structures of the molecular scaffolds in the collection of molecular scaffolds;
identify represented chemical structure fragments corresponding to chemical structure fragments from the set of common chemical structure fragments that are represented in the in-progress chemical structure;
identify a review portion of the amended in-progress chemical structure for comparison with a collection of stored molecular scaffolds, wherein the review portion comprises at least a portion of the represented chemical structure fragments based at least in part on their proximity to the point of amendment;
identify, by comparing the review portion to the collection of stored molecular scaffolds, one or more candidate molecular scaffolds, wherein each molecular scaffold of the one or more identified candidate molecular scaffolds is determined to, upon one or both of (i) appending to the review portion of the in-progress chemical structure and (ii) replacing or partially replacing the review portion of the in-progress chemical structure, provide at least a portion of a molecular scaffold from the collection of molecular scaffolds;
provide the one or more identified candidate molecular scaffolds for presentation on the graphical display as option(s) for selection by a user in creating the graphical representation of the chemical structure,
wherein providing the one or more candidate molecular scaffolds for presentation on the graphical display comprises visually rendering at least one of the candidate molecular scaffolds as an extension of the in-progress chemical structure;
receive an indication of user selection of a selected molecular scaffold of the one or more identified candidate molecular scaffolds provided; and
append the selected molecular scaffold to the review portion of the in-progress chemical structure or replace or partially replace the review portion of the in-progress chemical structure with the selected molecular scaffold, thereby updating the representation of the in-progress chemical structure.

32. The apparatus of claim 31, wherein the review portion comprises a predetermined threshold number of chemical structure fragments.

33. An apparatus for creating a graphical representation of a chemical structure using a draw-ahead feature, the apparatus comprising:
a memory for storing a set of instructions; and
a processor for executing the set of instructions, wherein the instructions, when executed, cause the processor to:
provide a representation of at least a portion of an in-progress chemical structure for presentation on a graphical display;
receive an input corresponding to an amendment to the portion of the in-progress chemical structure;
identify a review portion of the amended in-progress chemical structure for comparison with a collection of stored molecular scaffolds;
identify, by comparing the review portion to the collection of stored molecular scaffolds, one or more candidate molecular scaffolds, wherein each molecular scaffold of the one or more identified candidate molecular scaffolds is determined to, upon one or both of (i) appending to the review portion of the in-progress chemical structure and (ii) replacing or partially replacing the review portion of the in-progress chemical structure, provide at least a portion of a molecular scaffold from the collection of molecular scaffolds, wherein identifying the one or more candidate molecular scaffolds comprises, iteratively:
creating a modified review portion wherein the modified review portion is the review portion with one or more additional elements added and/or removed;
identifying one or more partially matching molecular scaffolds from the collection of molecular scaffolds by determining that the modified review portion is be a sub-structure of the partially matching molecular scaffold; and
for each partially matching molecular scaffold, identifying one or more respective candidate molecular scaffolds, wherein each of the one or more respective candidate molecular scaffolds is a sub-structure of the partially matching molecular scaffold distinct from the modified review portion;
provide the one or more identified candidate molecular scaffolds for presentation on the graphical display as option(s) for selection by a user in creating the graphical representation of the chemical structure, wherein providing the one or more candidate molecular scaffolds for presentation on the graphical display comprises visually rendering at least one of the candidate molecular scaffolds as an extension of the in-progress chemical structure;

receive an indication of user selection of a selected molecular scaffold of the one or more identified candidate molecular scaffolds provided; and append the selected molecular scaffold to the review portion of the in-progress chemical structure or replace or partially replace the review portion of the in-progress chemical structure with the selected molecular scaffold, thereby updating the representation of the in-progress chemical structure.

* * * * *